United States Patent
Park et al.

(10) Patent No.: US 8,329,953 B2
(45) Date of Patent: Dec. 11, 2012

(54) CYCLOPENTAPHENANTHRENE-BASED COMPOUND AND ORGANIC ELECTROLUMINESCENT DEVICE USING THE SAME

(75) Inventors: Sang-Hoon Park, Yongin-si (KR); Che-Un Yang, Yongin-si (KR); Jong-Jin Park, Yongin-si (KR); Jhun-Mo Son, Yongin-si (KR); O-Hyun Kwon, Yongin-si (KR); Yu-Jin Kim, Yongin-si (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 15 days.

(21) Appl. No.: 12/849,949

(22) Filed: Aug. 4, 2010

(65) Prior Publication Data

US 2010/0298607 A1 Nov. 25, 2010

Related U.S. Application Data

(62) Division of application No. 11/812,260, filed on Jun. 15, 2007, now Pat. No. 7,781,579.

(30) Foreign Application Priority Data

Jun. 15, 2006 (KR) .................. 10-2006-0053900
Nov. 17, 2006 (KR) .................. 10-2006-0113901

(51) Int. Cl.
*C07D 413/02* (2006.01)
*C07D 403/10* (2006.01)
*H01J 1/62* (2006.01)
*H01J 63/04* (2006.01)

(52) U.S. Cl. .................. 564/426; 564/427; 564/429

(58) Field of Classification Search .................. 564/426, 564/427, 429

See application file for complete search history.

(56) References Cited

U.S. PATENT DOCUMENTS

| 4,356,429 A | 10/1982 | Tang |
| 4,885,211 A | 12/1989 | Tang et al. |
| 5,151,629 A | 9/1992 | VanSlyke |

FOREIGN PATENT DOCUMENTS

JP   11-003782   1/1999

OTHER PUBLICATIONS

Yoshiyuki Kuwabara et al., "Thermally Stable Multilayered Organic Electroluminescent Devices Using Novel Starburst Molecules, 4,4',4" -Tri(N-carbazolyl)triphenylamine (TCTA) and 4,4',4"-Tris(3-methylphenlphenyl-amino)triphenylamine (m-MTDATA), as Hole-Transport Materials", Adv. Mater. 1994, 6, No. 9, pp. 677-679.

*Primary Examiner* — Kahsay T Habte
(74) *Attorney, Agent, or Firm* — Robert E. Bushnell, Esq.

(57) ABSTRACT

Provided are a cyclopentaphenanthrene-based compound and an organic EL device using the same. The cyclopentaphenanthrene-based compound is easy to prepare and excellent in solubility, color purity, and color stability. The cyclopentaphenanthrene-based compound is useful as a material for forming an organic layer, in particular, a light-emitting layer in an organic EL device, and as an organic dye or an electronic material such as a nonlinear optical material.

4 Claims, 3 Drawing Sheets

CYCLOPENTAPHENANTHRENE-BASED COMPOUND AND ORGANIC ELECTROLUMINESCENT DEVICE USING THE SAME

CROSS-REFERENCE TO RELATED PATENT APPLICATION AND CLAIM OF PRIORITY

This application makes reference to, incorporates the same herein and claims priority under 35 U.S.C. §§119 and 120 from Korean Patent Application Nos. 10-2006-0053900, filed on Jun. 15, 2006 and 10-2006-0113901, filed on Nov. 17, 2006, in the Korean Intellectual Property Office, the disclosure of which is incorporated herein in its entirety by reference. Furthermore, this application is filed pursuant to 35 U.S.C. §121 as a Divisional application of Applicants' patent application Ser. No. 11/812,260 filed in the U.S. Patent & Trademark Office on 15 Jun. 2007, and assigned to the assignee of the present invention. All benefits accruing under 35 U.S.C. §120 from the aforesaid present application Ser. No. 11/812,260 are also claimed.

BACKGROUND OF THE INVENTION

1. Field of the Invention

The present invention relates to a cyclopentaphenanthrene-based compound and to an organic electroluminescent device using the same. More particularly, the present invention relates to a cyclopentaphenanthrene-based compound and to an organic electroluminescent device including an organic layer made of the cyclopentaphenanthrene-based compound.

2. Description of the Related Art

Organic electroluminescent (EL) devices (also referred to as organic light-emitting devices) are active emission display devices that emit light by recombination of electrons and holes in a thin layer (hereinafter, referred to as "organic layer") made of a fluorescent or phosphorescent organic compound when a current is applied to the organic layer. The organic EL devices have advantages such as lightweight, simple constitutional elements, easy fabrication process, superior image quality, and wide viewing angle. In addition, the organic EL devices can perfectly create dynamic images, achieve high color purity, and have electrical properties suitable for portable electronic equipment due to low power consumption and low driving voltage.

Eastman Kodak Co. developed an organic EL device of a multi-layered structure using an aluminum quinolinol complex layer and a triphenylamine derivative layer (U.S. Pat. No. 4,885,211), and an organic EL device including an organic light-emitting layer made of a low molecular weight material capable of covering a broad emission wavelength range from UV to visible light (U.S. Pat. No. 5,151,629).

Light-emitting devices are self-emission devices and have advantages of a wide viewing angle, good contrast, and rapid response speed. The light-emitting devices can be classified into inorganic light-emitting devices including a light-emitting layer made of an inorganic compound and organic light-emitting devices (OLEDs; also referred to as "organic electroluminescent devices" (organic EL devices)) including a light-emitting layer made of an organic compound. The OLEDs show better brightness, driving voltage, and response speed characteristics and can achieve polychromatic changes, compared to inorganic light-emitting devices, and thus there have been many researches about OLEDs.

Generally, OLEDs have a stacked structure of an anode, an organic light-emitting layer, and a cathode. OLEDs may also have various structures such as anode/hole injection layer/hole transport layer/light-emitting layer/electron transport layer/electron injection layer/cathode or anode/hole injection layer/hole transport layer/light-emitting layer/hole blocking layer/electron transport layer/electron injection layer/cathode.

A material used in OLEDs can be divided into a vacuum deposition material and a solution coating material according to a method of forming an organic layer. The vacuum deposition material must have a vapor pressure of $10^{-6}$ torr or more at 500° C. or less, and may be a low molecular weight material with a molecular weight of 1200 or less. The solution coating material must have high solubility in a solvent to prepare a solution, and mainly includes an aromatic or heterocyclic compound.

In the case of manufacturing an OLED using a vacuum deposition process, manufacturing costs increase due to the use of a vacuum system. In the case of using a shadow mask to form pixels for a natural color display, it is difficult to obtain high resolution pixels. On the other hand, in the case of manufacturing an OLED using a solution coating process such as inkjet printing, screen printing, or spin coating, manufacturing is easy, manufacturing costs are low, and a relatively good resolution can be achieved as compared to the case of using a shadow mask.

However, thermal stability, color purity, etc. of light-emitting molecules of materials that can be used in the solution coating process are inferior to those that can be used in the vacuum deposition process. Even when the light-emitting molecules of the materials that can be used in the solution coating process are excellent in thermal stability, color purity, etc., the materials may be crystallized to grow a crystal size corresponding to a visible light wavelength range after they are made into an organic layer, thereby scattering visible light, resulting in turbidity phenomenon, and pin holes may be formed, thereby causing device degradation.

Japanese Patent Laid-Open Publication No. 1999-003782 discloses an anthracene compound substituted by two naphthyl groups which can be used in a light-emitting layer or a hole injection layer. However, the anthracene compound has poor solubility in a solvent, and an OLED using the compound exhibits unsatisfactory characteristics.

Therefore, there is still need to develop an organic EL device having improved driving voltage, brightness, efficiency and color purity, and good thermal stability.

SUMMARY OF THE INVENTION

The present invention provides a compound and an organic electroluminescent device using the compound.

The present invention provides a cyclopentaphenanthrene-based compound which is available for both dry and wet processes, and has good thermal stability, emission characteristics and charge transport, and an organic EL device using the same.

According to an aspect of the present invention, there is provided a cyclopentaphenanthrene-based compound represented by Formula 1 below:

<Formula 1>

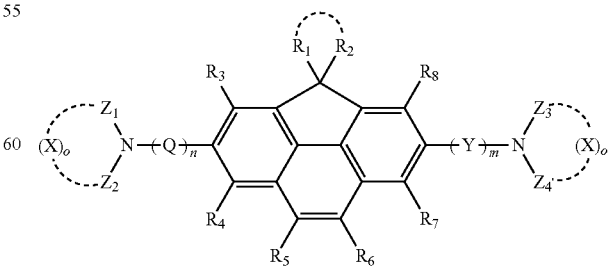

wherein Y and Q are the same or different and each is a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5;

n is an integer of 0 to 5;

$R_1$ and $R_2$ are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, $R_1$ and $R_2$ may be linked together, and $R_1$ and $R_2$, when linked together, form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring;

$R_3$, $R_4$, $R_5$, $R_6$, $R_7$, and $R_8$ are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($G_1$)($G_2$), or —Si($G_3$)($G_4$)($G_5$) where $G_1$, $G_2$, $G_3$, $G_4$, and $G_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group;

$Z_1$, $Z_2$, $Z_3$, and $Z_4$ are the same or different and each is a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C2-C30 heteroaryl group, a substituted or unsubstituted C6-C30 aralkyl group, a substituted or unsubstituted C8-C30 allylaryl group, a substituted or unsubstituted C1-C20 alkylene group, a substituted or unsubstituted C6-C30 arylene group, or a substituted or unsubstituted C2-C30 heteroarylene group;

X is a single bond, —CH═CH—, —O—, —S—, —Se—, or —C(R' R")— where R' and R" are the same as $R_3$, or —(CH$_2$)$_p$— where p is an integer of 1 to 10; and o is 0 or 1.

$R_1$ and $R_2$ may be linked together to form one of rings represented by Formulae 2 through 5 below:

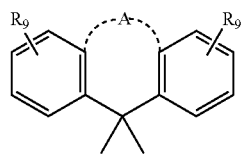

<Formula 2>

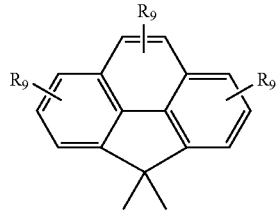

<Formula 3>

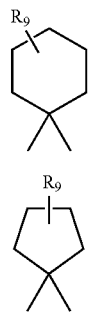

<Formula 4>

<Formula 5> wherein "$R_9$"s are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($G_1$)($G_2$), or —Si($G_3$)($G_4$)($G_5$) where $G_1$, $G_2$, $G_3$, $G_4$, and $G_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group; and A is a single bond, —O—, —S—, —(CH$_2$)$_s$— where s is an integer of 1 to 5.

According to an embodiment of the present invention, the cyclopentaphenanthrene-based compound of Formula 1 may be selected from compounds represented by Formulae 6 through 8 below:

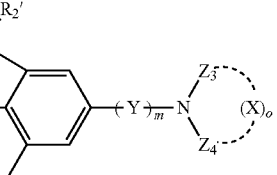

<Formula 6>

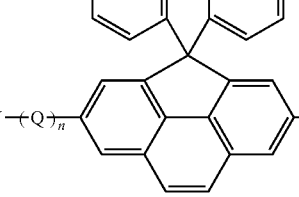

<Formula 7>

-continued

<Formula 8>

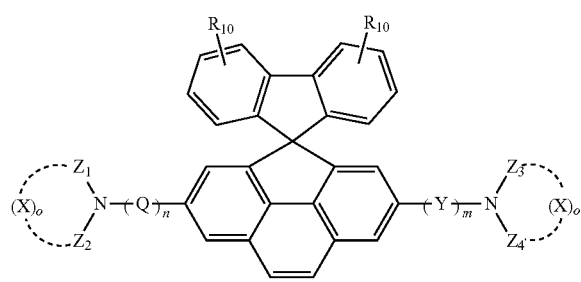

wherein Y and Q are the same or different and each is a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5;

n is an integer of 0 to 5;

$R_1'$ and $R_2'$ are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group;

$Z_1$, $Z_2$, $Z_3$, and $Z_4$ are the same or different and each is a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C2-C30 heteroaryl group, a substituted or unsubstituted C6-C30 aralkyl group, a substituted or unsubstituted C2-C30 allylaryl group, a substituted or unsubstituted C1-C20 alkylene group, a substituted or unsubstituted C6-C30 arylene group, or a substituted or unsubstituted C2-C30 heteroarylene group;

X is a single bond, —CH=CH—, —O—, —S—, —Se—, or —C(R'R")— where R' and R" are the same as $R_3$, or —(CH$_2$)$_p$— where p is an integer of 1 to 10;

o is 0 or 1; and

"$R_{10}$"s are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N(G$_1$)(G$_2$), or —Si(G$_3$)(G$_4$)(G$_5$) where G$_1$, G$_2$, G$_3$, G$_4$, and G$_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group.

According to another aspect of the present invention, there is provided an organic EL device including: a first electrode; a second electrode; and at least one organic layer interposed between the first electrode and the second electrode, the organic layer including the above-described organic light-emitting compound.

BRIEF DESCRIPTION OF THE DRAWINGS

Amore complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
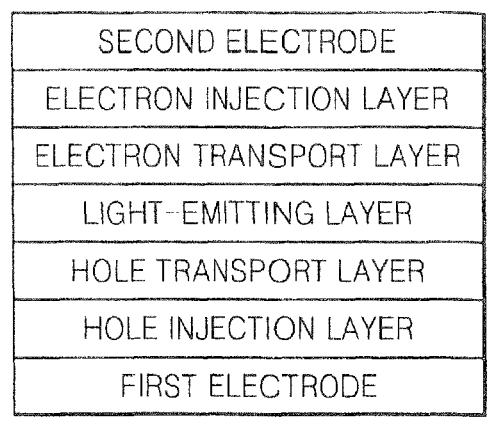
FIGS. 1A through 1C are schematic views illustrating organic EL devices according to embodiments of the present invention.

The present invention will now be described more fully with reference to the accompanying drawings, in which exemplary embodiments of the invention are shown.

The present invention provides a cyclopentaphenanthrene-based compound represented by Formula 1 below:

<Formula 1>

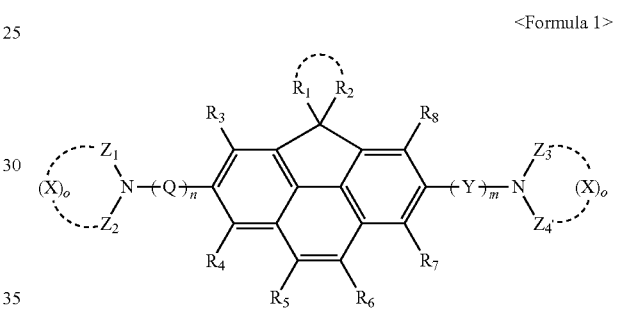

wherein Y and Q are the same or different and each is a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, preferably an integer of 0 to 2;

n is an integer of 0 to 5, preferably an integer of 0 to 2;

$R_1$ and $R_2$ are the same or different, and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, $R_1$ and $R_2$ may be linked together, and $R_1$ and $R_2$, when linked together, form a substituted or unsubstituted C3-C20 aliphatic ring, a substituted or unsubstituted C5-C30 heteroaliphatic ring, a substituted or unsubstituted C6-C30 aromatic ring, or a substituted or unsubstituted C2-C30 heteroaromatic ring;

$R_3$, $R_4$, $R_5$, $R_6$, $R_7$, and $R_8$ are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N(G$_1$)(G$_2$), or —Si(G$_3$)(G$_4$)(G$_5$) where G$_1$, G$_2$, G$_3$, G$_4$, and G$_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group;

$Z_1$, $Z_2$, $Z_3$, and $Z_4$ are the same or different and each is a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C2-C30 heteroaryl group, a substituted or unsubstituted C6-C30 aralkyl group, a substituted or unsubstituted C8-C30 allylaryl group, a substituted or unsubstituted C1-C20 alkylene group, a substituted or unsubstituted C6-C30 arylene group, or a substituted or unsubstituted C2-C30 heteroarylene group;

X is a single bond, —CH=CH—, —O—, —S—, —Se—, or —C(R'R")— where R' and R" are the same as $R_3$, or —(CH$_2$)$_p$— where p is an integer of 1 to 10; and o is 0 or 1.

When $R_1$ and $R_2$ are linked together, $R_1$ and $R_2$ preferably form one represented by Formulae 2 through 5 below:

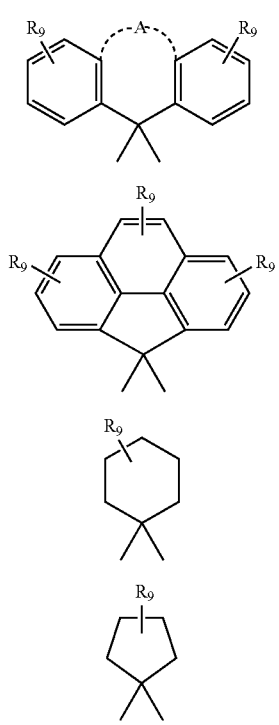

<Formula 2>

<Formula 3>

<Formula 4>

<Formula 5> wherein "$R_9$"s are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N(G$_1$)(G$_2$), or —Si(G$_3$)(G$_4$)(G$_5$) where G$_1$, G$_2$, G$_3$, G$_4$, and G$_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group; and A is a single bond, —O—, —S—, or —(CH$_2$)$_s$— where s is an integer of 1 to 5.

In particular, in the compounds of Formulae 1-5, $R_1$ through $R_9$ serve to enhance film processibility by increasing the solubility and amorphous property of the compounds.

The compound of Formula 1 according to the present invention may be selected from compounds represented by Formulae 6 through 8 below:

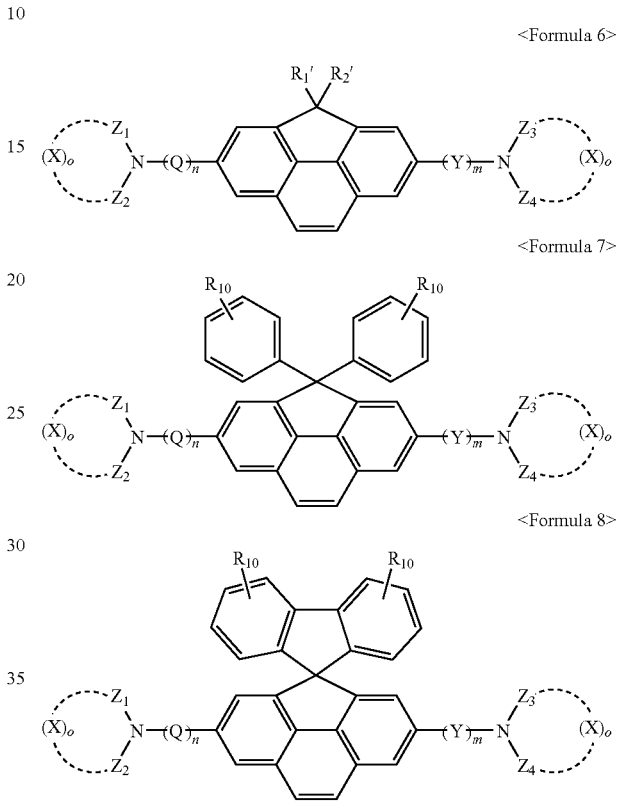

<Formula 6>

<Formula 7>

<Formula 8> wherein Y and Q are the same or different and each is a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5, preferably an integer of 0 to 2;

n is an integer of 0 to 5, preferably an integer of 0 to 2;

$R_1'$ and $R_2'$ are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, or a substituted or unsubstituted C2-C30 heteroaryl group;

$Z_1$, $Z_2$, $Z_3$, and $Z_4$ are the same or different and each is a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C2-C30 heteroaryl group, a substituted or unsubstituted C6-C30 aralkyl group, a substituted or unsubstituted C2-C30 allylaryl group, a substituted or unsubstituted C1-C20 alkylene group, a substituted or unsubstituted C6-C30 arylene group, or a substituted or unsubstituted C2-C30 heteroarylene group;

X is a single bond, —CH═CH—, —O—, —S—, —Se—, or —C(R'R")— where R' and R" are the same as $R_3$, or —(CH$_2$)$_p$— where p is an integer of 1 to 10;

o is 0 or 1; and

"$R_{10}$"s are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N(G$_1$)(G$_2$), or —Si(G$_3$)(G$_4$)(G$_5$) where G$_1$, G$_2$, G$_3$, G$_4$, and G$_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group.

In the above formula, the "aryl group" refers to a monovalent group having an aromatic ring system and may contain one, two or more ring systems. The two or more ring systems may be attached to each other or may be fused. The "heteroaryl group" refers to an aryl group in which at least one carbon atom is substituted by at least one selected from the group consisting of N, O, S, and P.

The "cycloalkyl group" refers to an alkyl group having a ring system, and the "heterocycloalkyl group" refers to a cycloalkyl group in which at least one carbon atom is substituted by at least one selected from the group consisting of N, O, S, and P.

In the above formula, the alkyl group, the alkoxy group, the aryl group, the heteroaryl group, the cycloalkyl group, and the heterocycloalkyl group may be substituted by at least one substituent selected from the group consisting of —F; —Cl; —Br; —CN; —NO$_2$; —OH; a C1-C20 alkyl group which is unsubstituted or substituted by —F, —Cl, —Br, —CN, —NO$_2$, or —OH; a C1-C20 alkoxy group which is unsubstituted or substituted by —F, —Cl, —Br, —CN, —NO$_2$, or —OH; a C6-C30 aryl group which is unsubstituted or substituted by a C1-C20 alkyl group, a C1-C20 alkoxy group, —F, —Cl, —Br, —CN, —NO$_2$, or —OH; a C2-C30 heteroaryl group which is unsubstituted or substituted by a C1-C20 alkyl group, a C1-C20 alkoxy group, —F, —Cl, —Br, —CN, —NO$_2$, or —OH; a C5-C20 cycloalkyl group which is unsubstituted or substituted by a C1-C20 alkyl group, a C1-C20 alkoxy group, —F, —Cl, —Br, —CN, —NO$_2$, or —OH; a C2-C30 heterocycloalkyl group which is unsubstituted or substituted by a C1-C20 alkyl group, a C1-C20 alkoxy group, —F, —Cl, —Br, —CN, —NO$_2$, or —OH; and —N(G$_6$)(G$_7$). At this time, G$_6$ and G$_7$ are the same or different and each may be a hydrogen; a C1-C10 alkyl group; or a C6-C30 aryl group substituted by a C1-C10 alkyl group.

In more detail, $R_1$-$R_{10}$ are the same or different and each may be selected from the group consisting of a hydrogen, a halogen, a cyano group, a hydroxyl group, a substituted or unsubstituted C1-C10 alkyl group, a substituted or unsubstituted C1-C10 alkoxy group, and a substituted or unsubstituted group as follows: a phenyl group, a biphenyl group, a pentalenyl group, an indenyl group, a naphthyl group, a biphenylenyl, an anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxiranyl group, a pyrrolidinyl group, a pyrazolidinyl group, an imidazolidinyl group, a piperidinyl group, a piperazinyl group, a morpholinyl group, a di(C6-C30 aryl)amino group, a tri(C6-C30 aryl)silyl group, or a derivative thereof.

The term "derivative(s) refers to a compound derived or obtained from another and containing essential elements of the above-illustrated group(s). Preferably, the term "derivative(s)" refers to the above-illustrated group(s) wherein at least one hydrogen is substituted by a substituent as described above.

The cyclopentaphenanthrene-based compound of the present invention may be selected from the group consisting of compounds represented by Formulae 9 through 46 below, but is not limited thereto:

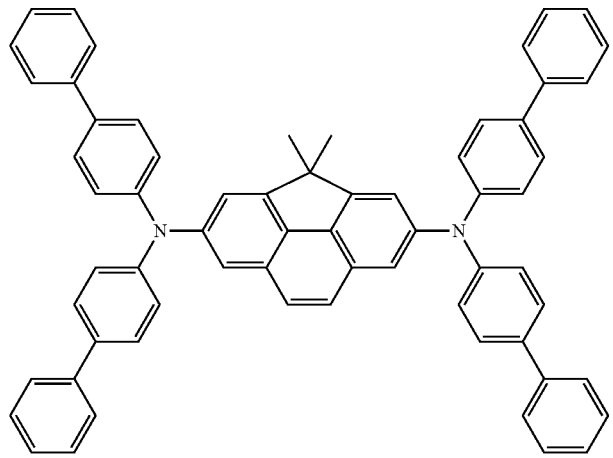

<Formula 9>

<Formula 10>
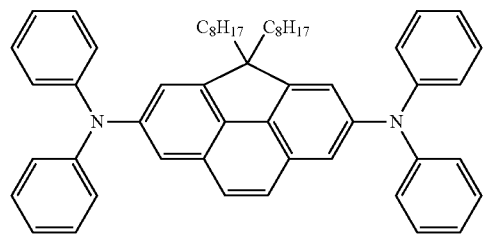
<Formula 11>
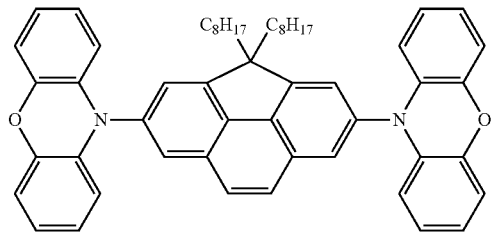
<Formula 12>
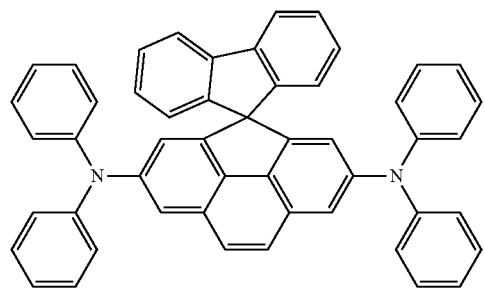
<Formula 13>
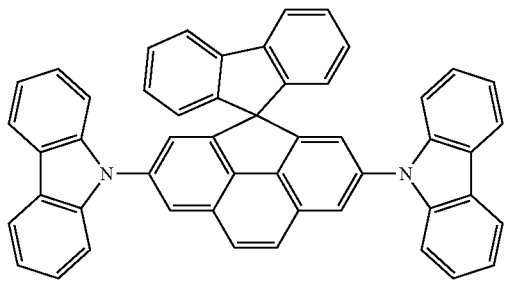
<Formula 14>
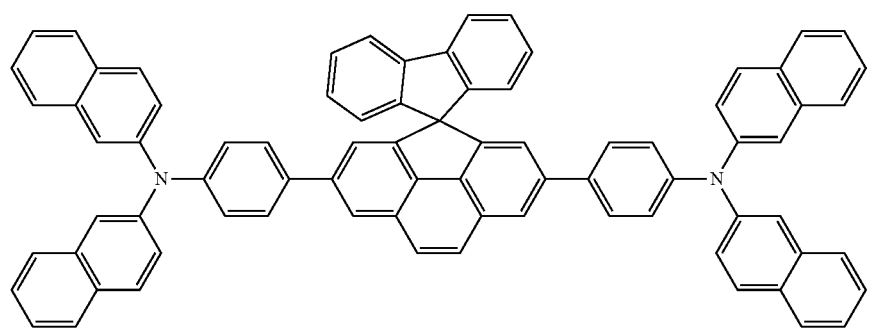
<Formula 15>
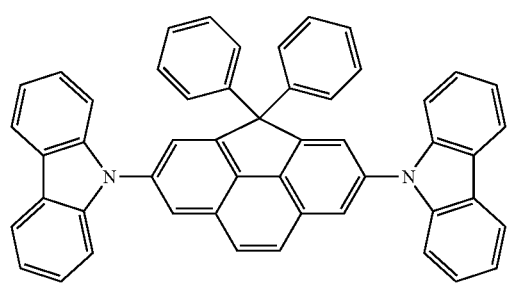
<Formula 16>
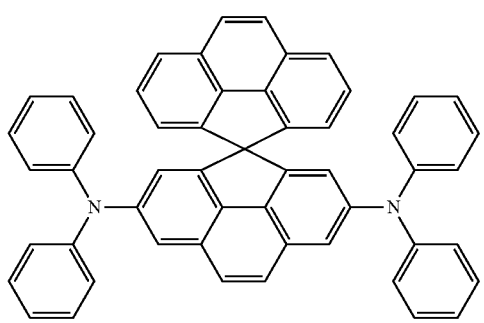

<Formula 17>
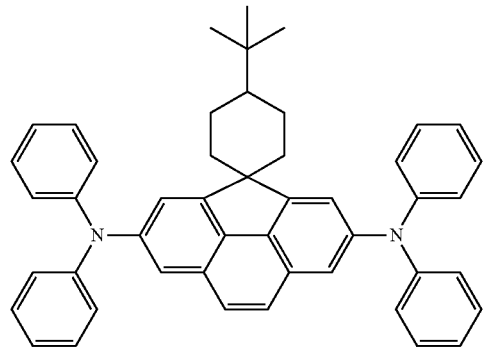
<Formula 18>
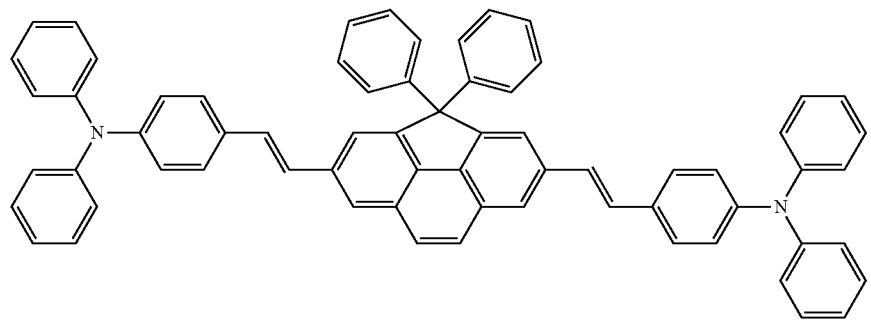
<Formula 19>
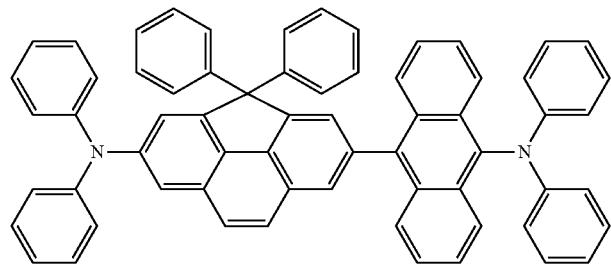
<Formula 20>
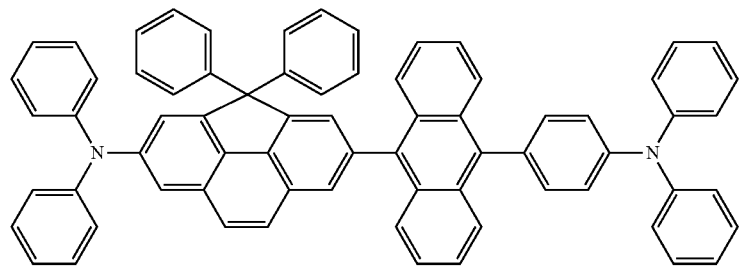
<Formula 21>
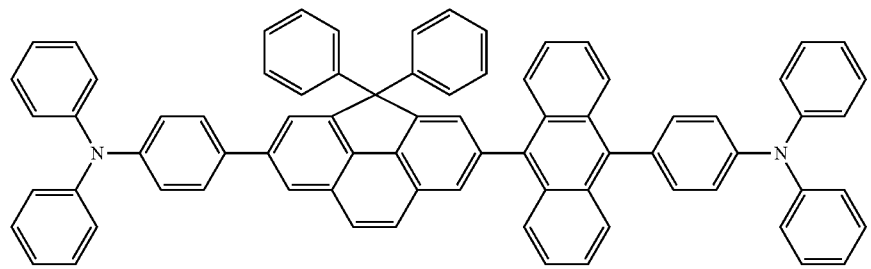

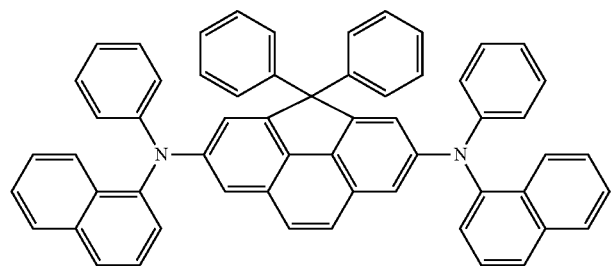
<Formula 22>
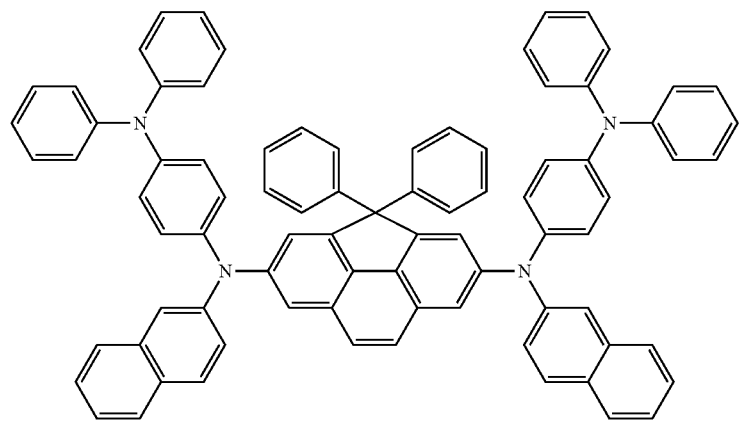
<Formula 23>
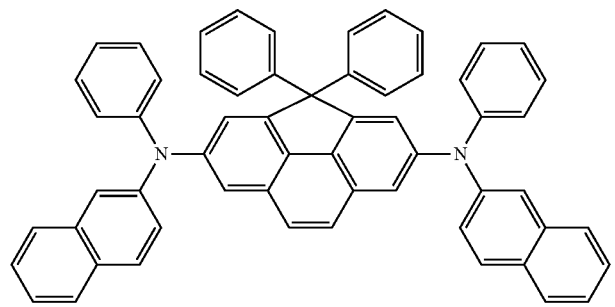
<Formula 24>
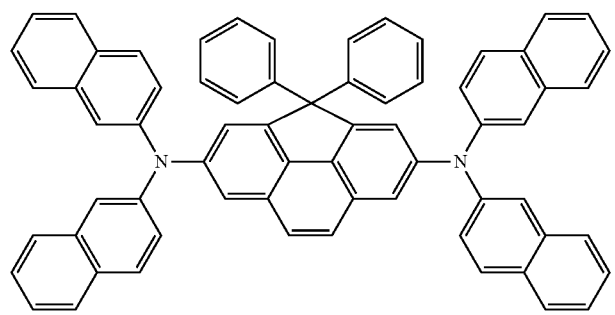
<Formula 25>

<Formula 26>
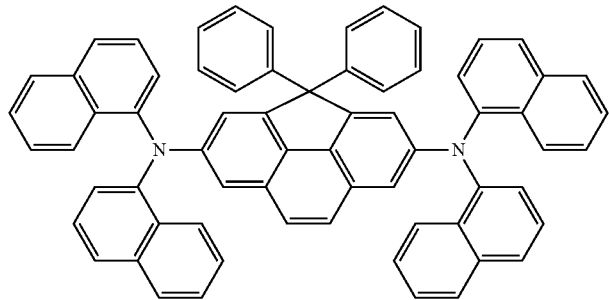
<Formula 27>
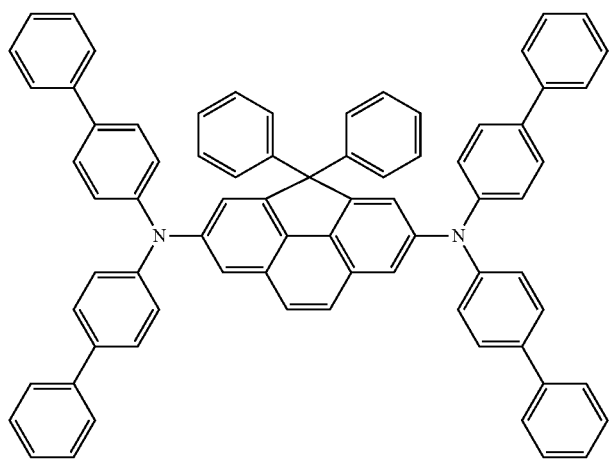
<Formula 28>
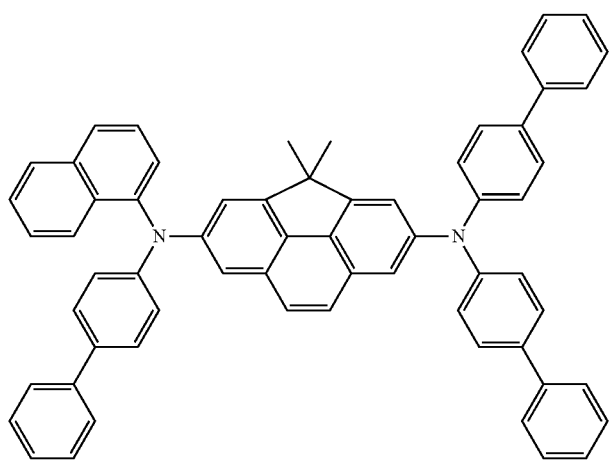

<Formula 29>
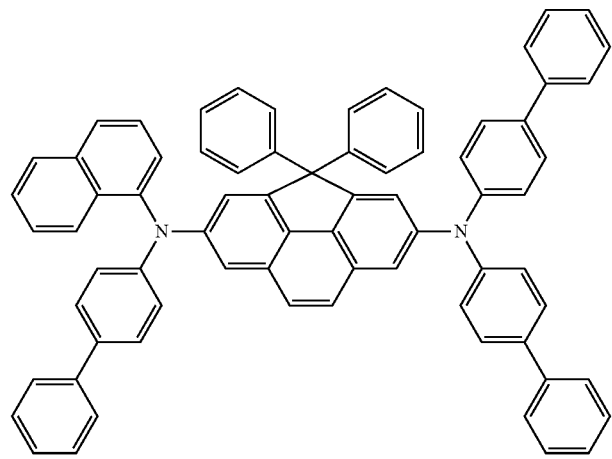
<Formula 30>
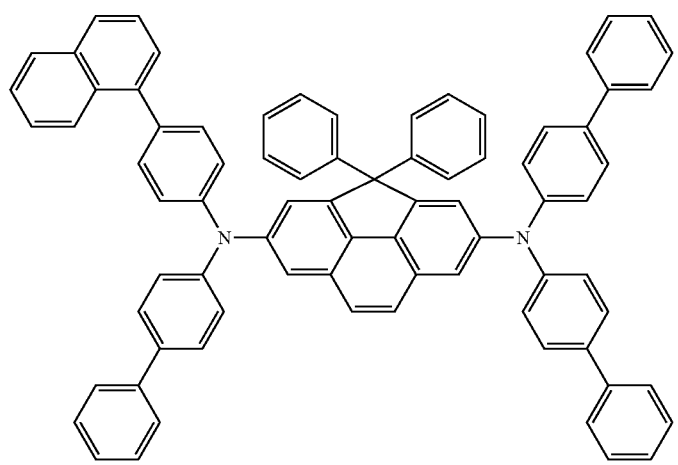
<Formula 31>
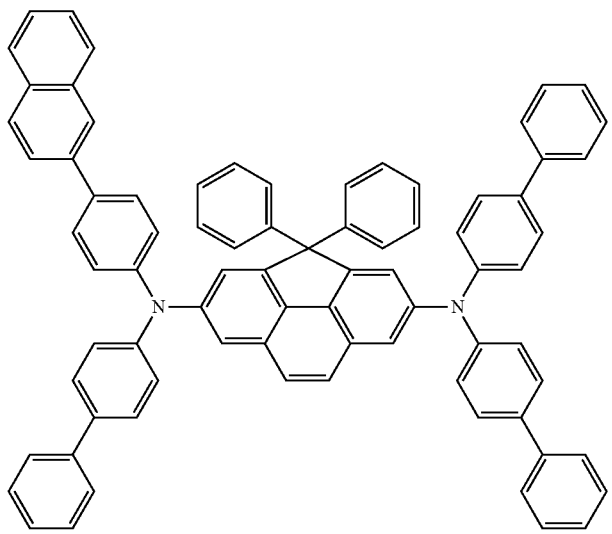

<Formula 32>
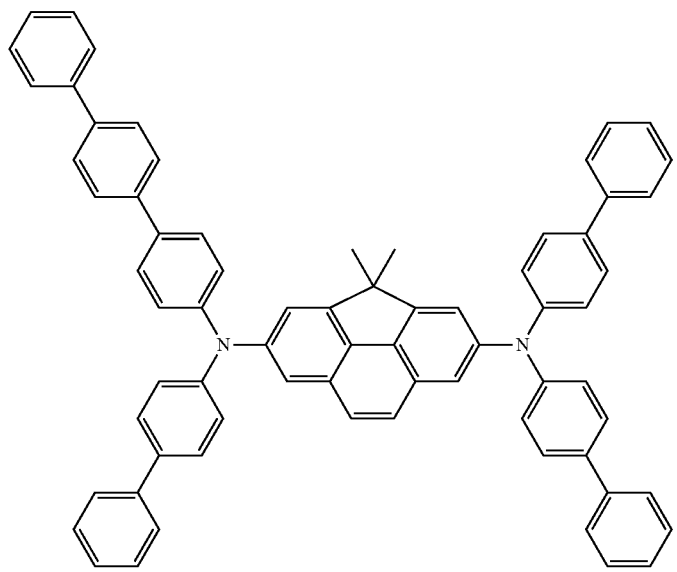
<Formula 33>
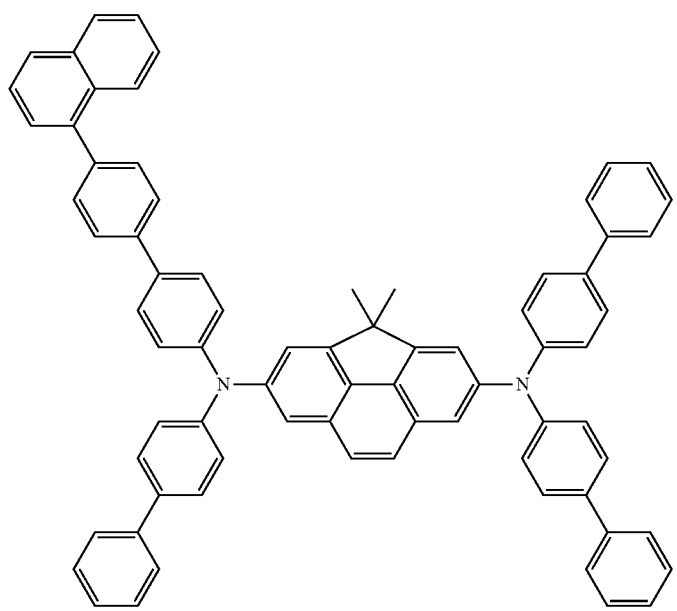
<Formula 34>
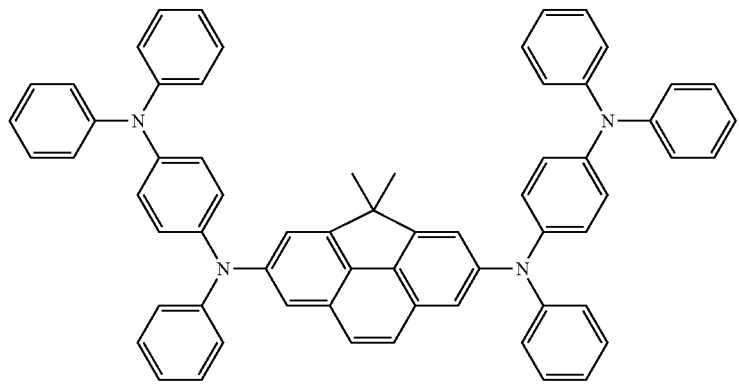

<Formula 35>
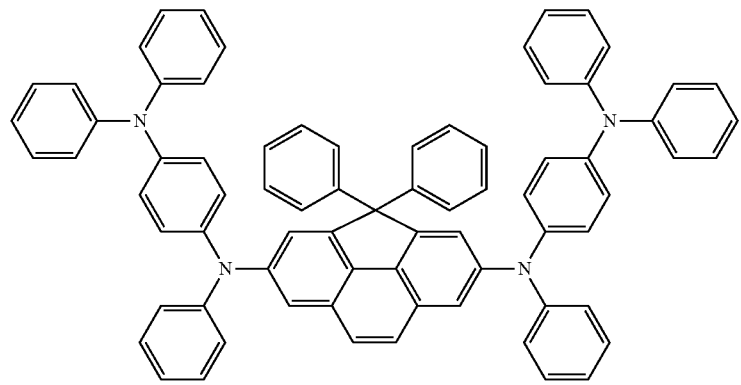
<Formula 36>
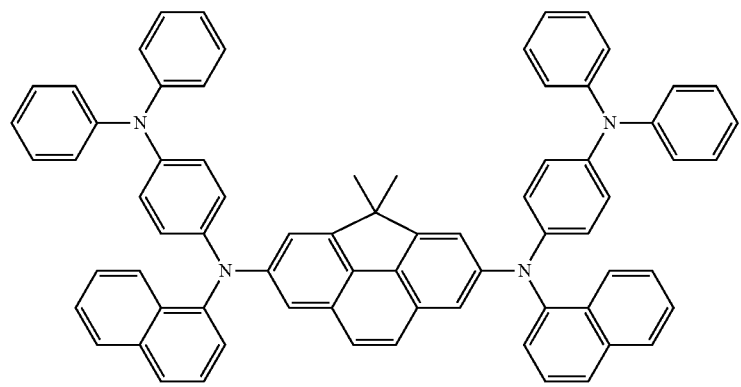
<Formula 37>
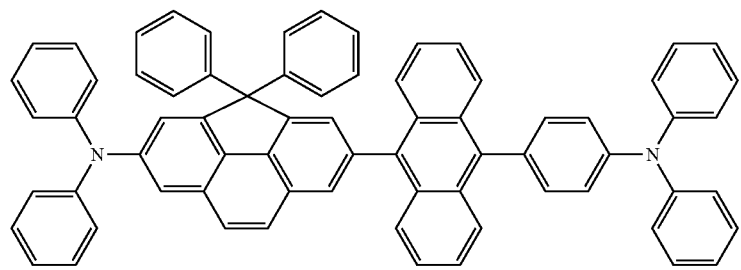
<Formula 38>
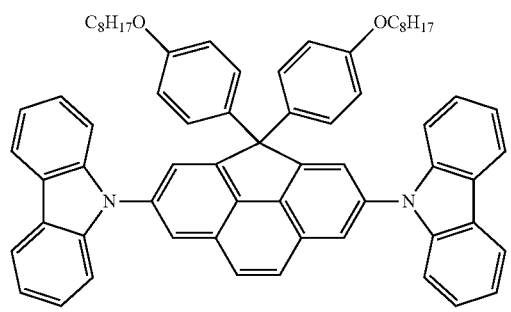

-continued
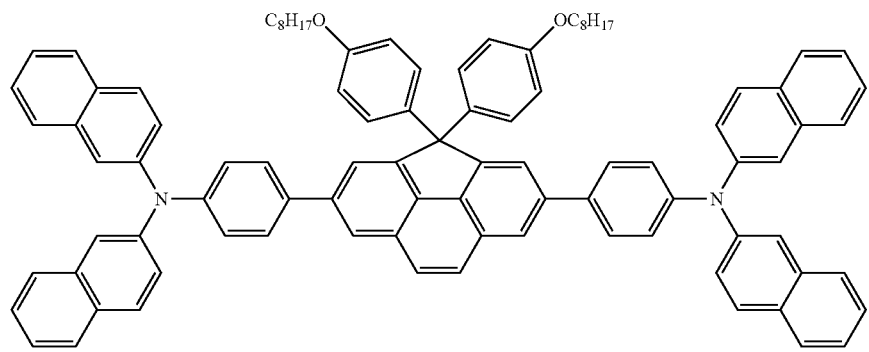
<Formula 39>
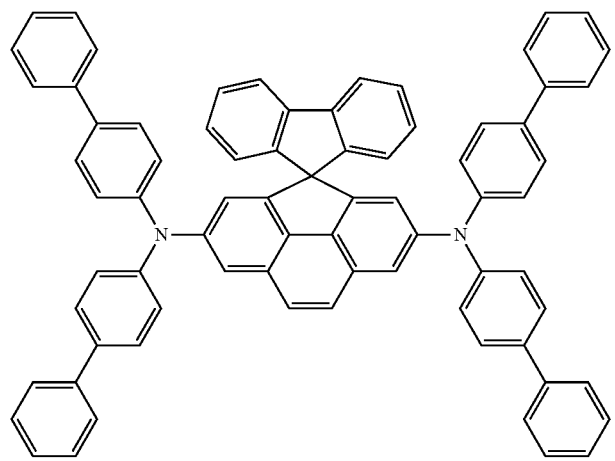
<Formula 40>
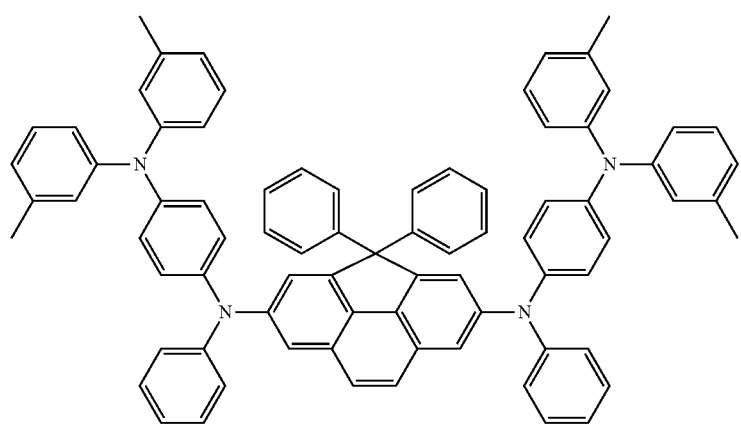
<Formula 41>

-continued
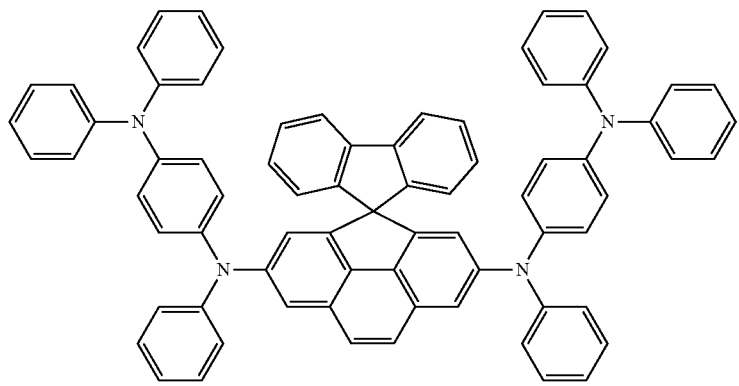
<Formula 42>
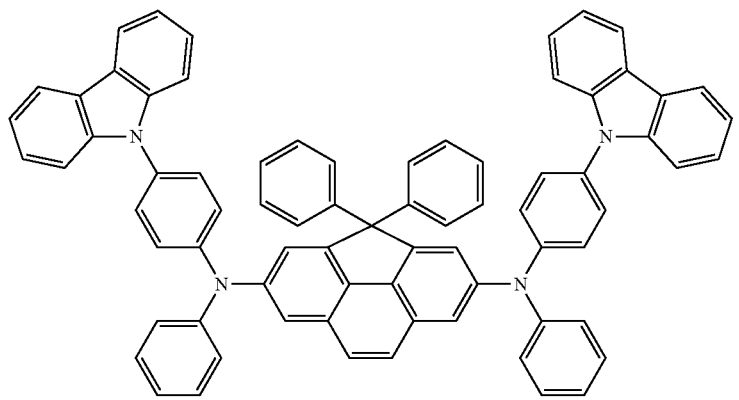
<Formula 43>
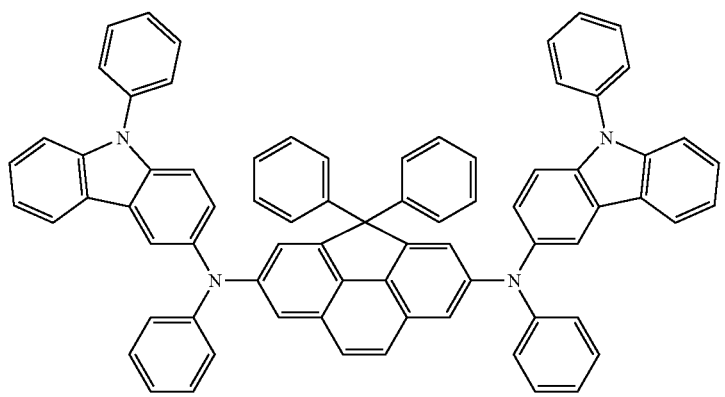
<Formula 44>
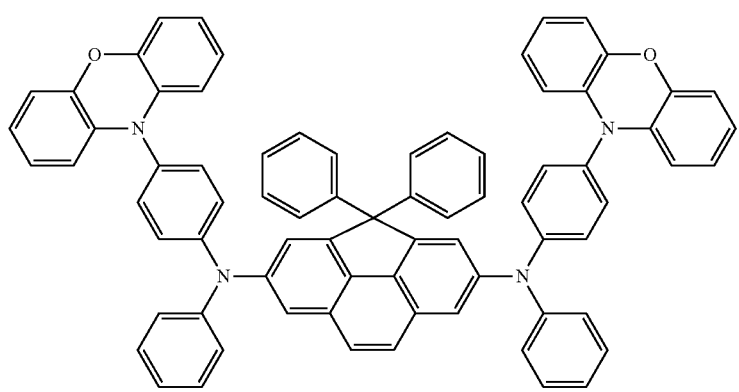
<Formula 45>

<Formula 46>

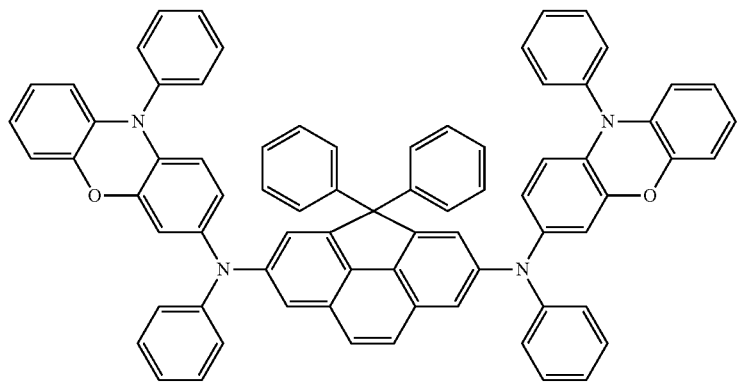

The compound of Formula 1 according to the present invention can be synthesized using a common synthesis method. For a detailed synthesis method of the compound of the present invention, reference will be made to the reaction schemes in the following synthesis examples.

The present invention also provides an organic EL device including:
 a first electrode;
 a second electrode; and
 an organic layer interposed between the first electrode and the second electrode, the organic layer including at least one compound represented by Formula 1 above.

The compound of Formula 1 above is suitable for an organic layer of an organic EL device, in particular, a light-emitting layer (also referred to as an emissive layer), a hole injection layer, or a hole transport layer.

An organic EL device according to the present invention includes a compound which has good solubility and thermal stability and can form a stable organic layer, and thus, can provide a good driving voltage and enhanced emission characteristics (e.g., color purity), unlike a conventional organic EL device including a less stable organic layer when manufactured using a solution coating process.

The organic EL device according to the present invention can be variously structured. That is, the organic EL device may further include at least one layer selected from the group consisting of a hole injection layer, a hole transport layer, a hole blocking layer, an electron blocking layer, an electron transport layer, and an electron injection layer, between the first electrode and the second electrode.

Figure 1B:
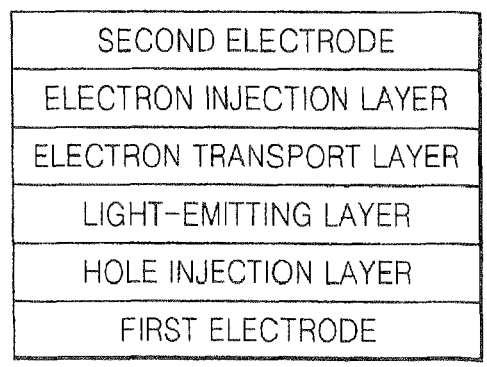
Figure 1C:
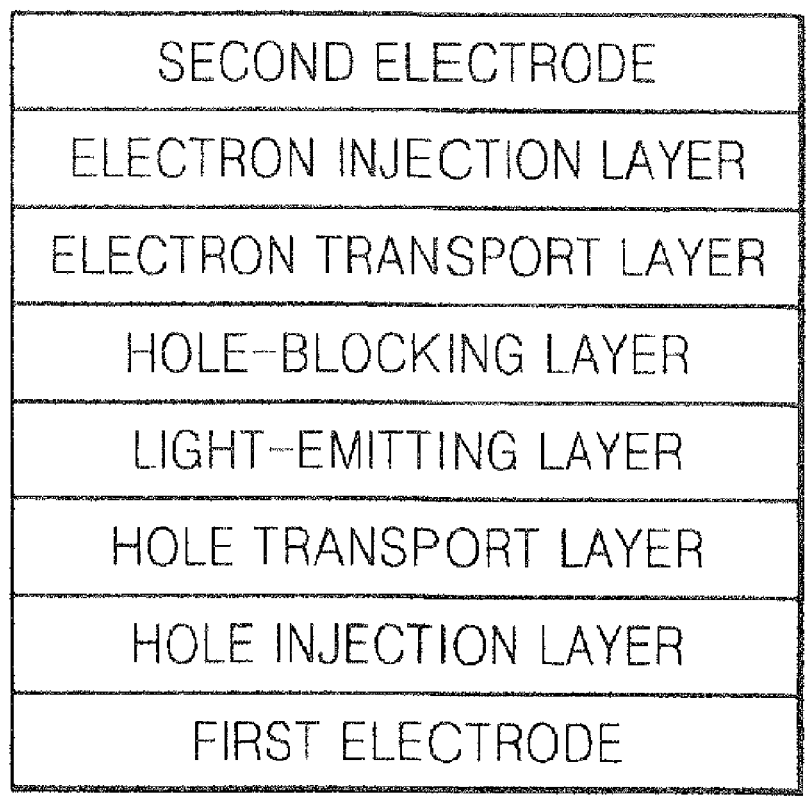

In more detail, embodiments of the organic EL device according to the present invention are illustrated in FIGS. 1A, 1B, and 1C. Referring to FIG. 1A, an organic EL device has a stacked structure of first electrode/hole injection layer/hole transport layer/light-emitting layer/electron transport layer/electron injection layer/second electrode. Referring to FIG. 1B, an organic EL device has a stacked structure of first electrode/hole injection layer/light-emitting layer/electron transport layer/electron injection layer/second electrode. Referring to FIG. 1C, an organic EL device has a stacked structure of first electrode/hole injection layer/hole transport layer/light-emitting layer/hole blocking layer/electron transport layer/electron injection layer/second electrode. At this time, at least one of the light-emitting layer, the hole injection layer, and the hole transport layer may include the compound of Formula 1 of the present invention.

A light-emitting layer of the organic EL device according to the present invention may include a red, green, blue, or white phosphorescent or fluorescent dopant. The phosphorescent dopant may be an organometallic compound including at least one element selected from the group consisting of Ir, Pt, Os, Ti, Zr, Hf, Eu, Tb, and Tm.

Hereinafter, a method of manufacturing an organic EL device according to the present invention will be described with reference to FIG. 1C.

First, a first electrode material with a high work function is formed on a substrate using deposition or sputtering to form a first electrode. The first electrode may be an anode. Here, the substrate may be a substrate commonly used in organic EL devices. Preferably, the substrate may be a glass substrate or a transparent plastic substrate which is excellent in mechanical strength, thermal stability, transparency, surface smoothness, handling property, and water repellency. The first electrode material may be a material with good transparency and conductivity, e.g., indium tin oxide (ITO), indium zinc oxide (IZO), tin oxide ($SnO_2$), or zinc oxide (ZnO).

Next, a hole injection layer (HIL) may be formed on the first electrode using various methods such as vacuum deposition, spin-coating, casting, or Langmuir-Blodgett (LB) method.

In the case of forming the hole injection layer using a vacuum deposition process, the deposition conditions vary according to the type of a hole injection layer material, the structure and thermal characteristics of the hole injection layer, etc. However, it is preferred that the hole injection layer is deposited to a thickness of 10 Å to 5 μm at a deposition rate of 0.01 to 100 Å/sec, at a temperature of 100 to 500° C., in a vacuum level of $10^{-8}$ to $10^{-3}$ torr.

In the case of forming the hole injection layer using a spin-coating process, the coating conditions vary according to the type of a hole injection layer material, the structure and thermal characteristics of the hole injection layer, etc. However, it is preferred that the spin-coating is performed at a coating speed of about 2000 to 5000 rpm, and, after the spin-coating, a thermal treatment is performed at a temperature of about 80 to 200° C. for the purpose of solvent removal.

The hole injection layer material may be a compound of Formula 1 as described above. In addition, the hole injection layer material may be a known hole injection material, e.g., a phthalocyanine compound (e.g., copper phthalocyanine) disclosed in U.S. Pat. No. 4,356,429, a Starburst-type amine derivative (e.g., TCTA, m-MTDATA, or m-MTDAPB) disclosed in *Advanced Material*, 6, p. 677 (1994), or a soluble conductive polymer, e.g., Pani/DBSA (Polyaniline/Dodecylbenzenesulfonic acid), PEDOT/PSS (Poly(3,4-ethylenedioxythiophene)/Poly(4-styrenesulfonate)), Pani/CSA (Polyaniline/Camphor sulfonic acid), or PANI/PSS (Polyaniline/Poly(4-styrenesulfonate).

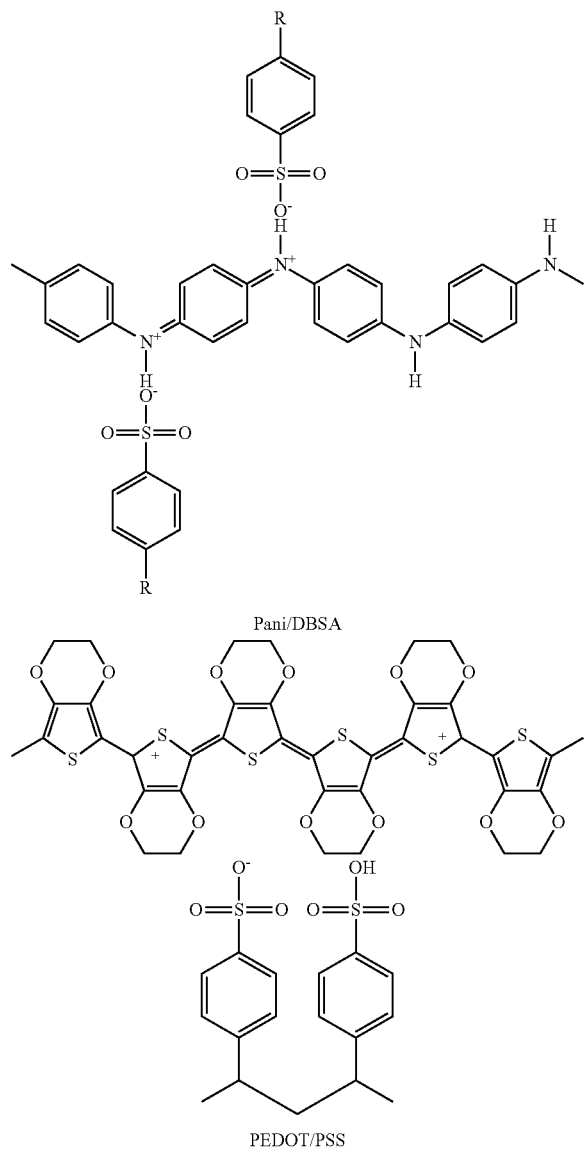

Pani/DBSA

PEDOT/PSS

The hole injection layer may be formed to a thickness of about 100 to 10,000 Å, preferably 100 to 1,000 Å. If the thickness of the hole injection layer is less than 100 Å, hole injection characteristics may be lowered. On the other hand, if the thickness of the hole injection layer exceeds 10,000 Å, a driving voltage may be increased.

Next, a hole transport layer (HTL) may be formed on the hole injection layer using various methods such as vacuum deposition, spin-coating, casting, or LB method. In the case of forming the hole transport layer using vacuum deposition or spin-coating, the deposition or coating conditions vary according to the type of a used compound, but are generally almost the same as those for the formation of the hole injection layer.

A hole transport layer material may be a compound of Formula 1 as described above. In addition, the hole transport layer material can be a known hole transport material, e.g., a carbazole derivative such as N-phenylcarbazole or polyvinylcarbazole; an amine derivative having an aromatic fused ring system such as N,N'-bis(3-methylphenyl)-N,N'-diphenyl-[1,1'-biphenyl]-4,4'-diamine (TPD) or N,N'-di(naphthalene-1-yl)-N,N'-diphenylbenzidine (α-NPD), etc.

The hole transport layer may be formed to a thickness of about 50 to 1,000 Å, preferably 100 to 600 Å. If the thickness of the hole transport layer is less than 50 Å, hole transport characteristics may be lowered. On the other hand, if the thickness of the hole transport layer exceeds 1,000 Å, a driving voltage may be increased.

Next, a light-emitting layer (EML) is formed on the hole transport layer using vacuum deposition, spin-coating, casting, or LB method. In the case of forming the light-emitting layer using vacuum deposition or spin-coating, the deposition or coating conditions vary according to the type of a used compound, but are generally almost the same as those for the formation of the hole injection layer.

The light-emitting layer may include a compound of Formula 1 as described above. At this time, a known fluorescent host material or a known dopant material suitable for the compound of Formula 1 may also be used. The compound of Formula 1 can be used as a phosphorescent host alone or in combination with CBP (4,4'-N,N'-dicarbazole-biphenyl), PVK (poly(n-vinylcarbazole)), etc. A red phosphorescent dopant (e.g., PtOEP, RD 61 (UDC)), a green phosphorescent dopant (e.g., Ir(PPy)$_3$ (PPy=2-phenylpyridine)), or a blue phosphorescent dopant (e.g., F$_2$Irpic) may be used as a phosphorescent dopant.

When the compound of Formula 1 is used as a dopant, the doping concentration of the dopant is not particularly limited. Generally, the content of the dopant is 0.01 to 15 parts by weight based on 100 parts by weight of a host. When the compound of Formula 1 is used as a single host, the doping concentration of a dopant is not particularly limited. Generally, the content of a dopant is 0.01 to 15 parts by weight based on 100 parts by weight of the host. When the compound of Formula 1 is used as a host in combination with another host, the content of the compound of Formula 1 is 30-99 parts by weight based on the total weight (100 parts by weight) of the hosts.

The light-emitting layer may be formed to a thickness of about 100 to 1,000 Å, preferably 200 to 600 Å. If the thickness of the light-emitting layer is less than 100 Å, emission characteristics may be lowered. On the other hand, if the thickness of the light-emitting layer exceeds 1,000 Å, a driving voltage may be increased.

In a case where the light-emitting layer includes a phosphorescent dopant, a hole blocking layer (HBL) may be formed on the hole transport layer using vacuum deposition, spin-coating, casting, or LB method, in order to prevent the diffusion of triplet excitons or holes into an electron transport layer. In the case of forming the hole blocking layer using vacuum deposition or spin coating, the deposition or coating conditions vary according to the type of a used compound, but are generally almost the same as those for the formation of the hole injection layer. An available hole blocking material may be an oxadiazole derivative, a triazole derivative, a phenanthroline derivative, BCP, an aluminum complex, etc.

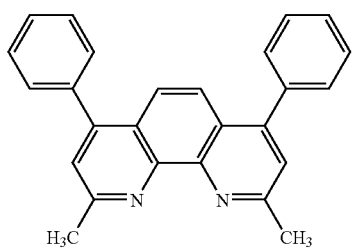

Phenanthroline-containing organic compound

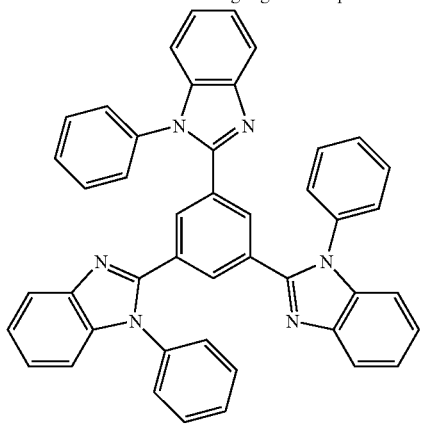

Imidazole-containing organic compound

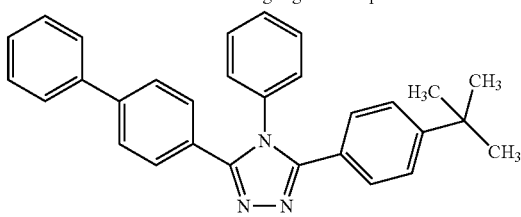

Triazole-containing organic compound

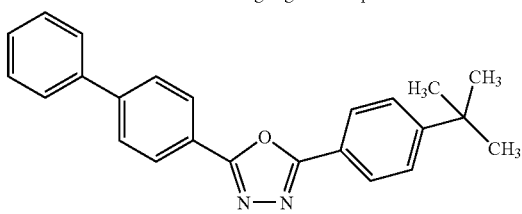

Oxadiazole-containing compound

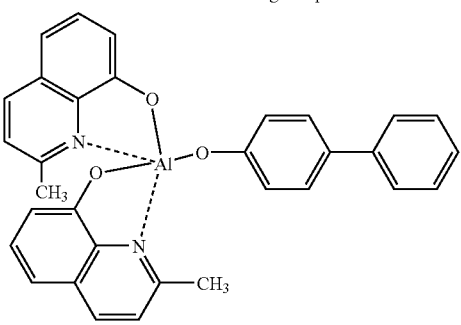

BAlq

The hole blocking layer may be formed to a thickness of about 50 to 1,000 Å, preferably 100 to 300 Å. If the thickness of the hole blocking layer is less than 50 Å, hole blocking characteristics may be lowered. On the other hand, if the thickness of the hole blocking layer exceeds 1,000 Å, a driving voltage may be increased.

Next, an electron transport layer (ETL) may be formed using various methods such as vacuum deposition, spin-coating, or casting. In the case of forming the electron transport layer using vacuum deposition or spin-coating, the deposition or coating conditions vary according to the type of a used compound, but are generally almost the same as those for the formation of the hole injection layer. An electron transport layer material serves to stably transport electrons from an electron donor electrode (a cathode) and may be a known material such as an oxazole-based compound, an isoxazole-based compound, a triazole-based compound, an isothiazole-based compound, an oxadiazole-based compound, a thiadiazole-based compound, a perylene-based compound, an aluminum complex (e.g.: Alq3 (tris(8-quinolinolato)-aluminum) BAlq, SAlq, or Almq3), a gallium complex (e.g.: Gaq'2OPiv, Gaq'2OAc, 2(Gaq'2)), etc.

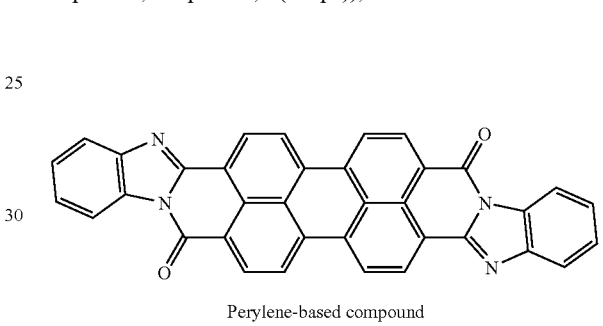

Perylene-based compound

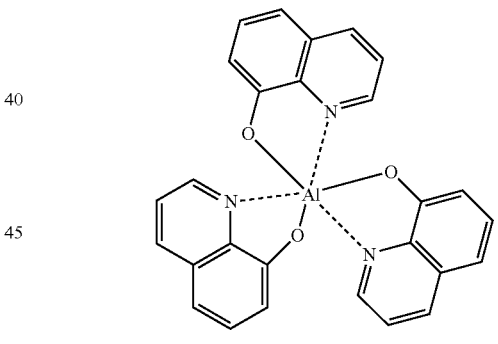

Alq3

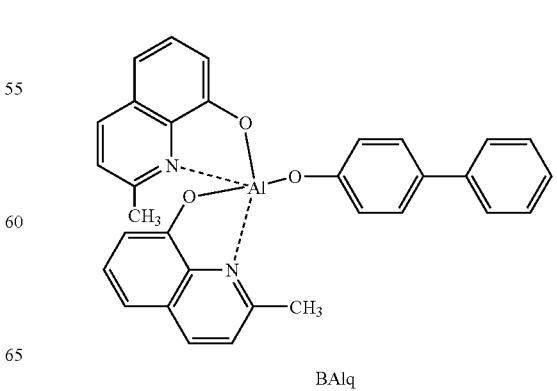

BAlq

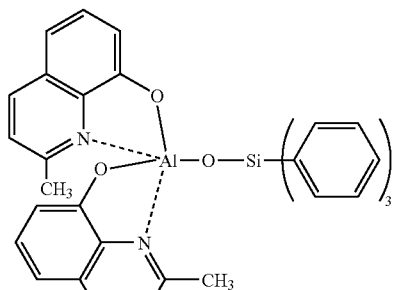

SAlq

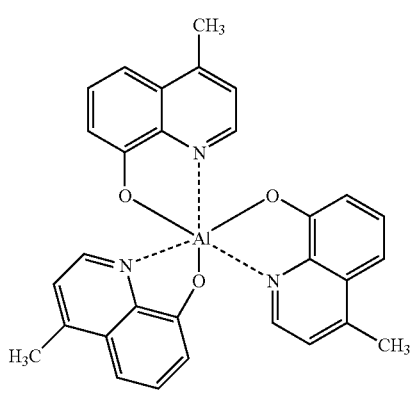

Almq3

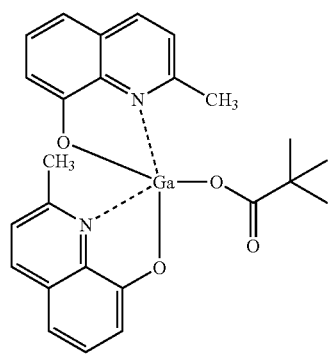

Gaq'2OPiv

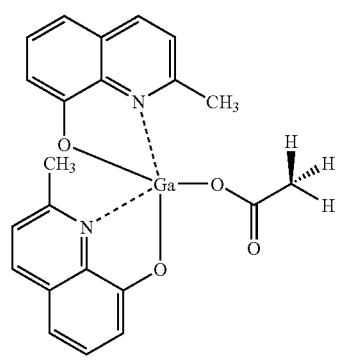

Gaq'2Oac

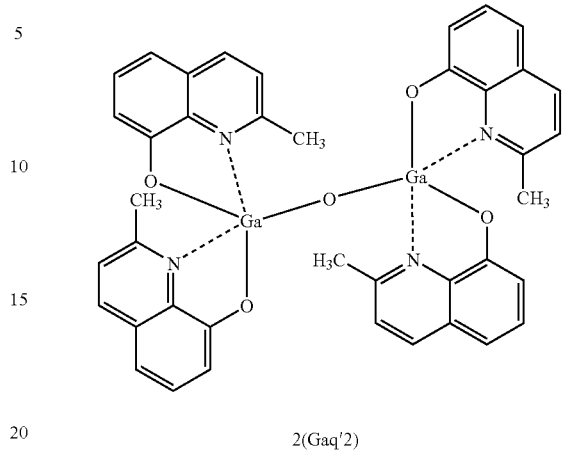

2(Gaq'2)

The electron transport layer may be formed to a thickness of about 100 to 1,000 Å, preferably 200 to 500 Å. If the thickness of the electron transport layer is less than 100 Å, electron transport characteristics may be lowered. On the other hand, if the thickness of the electron transport layer exceeds 1,000 Å, a driving voltage may be increased.

An electron injection layer (EIL) may be formed on the electron transport layer in order to facilitate the injection of electrons from a cathode into the light-emitting layer. An electron injection layer material is not particularly limited.

The electron injection layer material may be optionally selected from known materials such as LiF, NaCl, CsF, $Li_2O$, or BaO. The deposition conditions of the electron injection layer vary according to the type of a used compound, but are generally almost the same as those for the formation of the hole injection layer.

The electron injection layer may be formed to a thickness of about 1 to 100 Å, preferably 5 to 50 Å. If the thickness of the electron injection layer is less than 1 Å, electron injection characteristics may be lowered. On the other hand, if the thickness of the electron injection layer exceeds 100 Å, a driving voltage may be increased.

Finally, a second electrode is formed on the electron injection layer using vacuum deposition or sputtering. The second electrode may be used as a cathode. A material for forming the second electrode may be metal or alloy with a low work function, an electroconductive compound, or a mixture thereof. For example, the second electrode forming material may be lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode made of ITO or IZO to provide a front-emission type device.

Hereinafter, the present invention will be described more specifically with reference to the following working examples. However, the following examples are for illustrative purposes and are not intended to limit the scope of the invention.

EXAMPLES
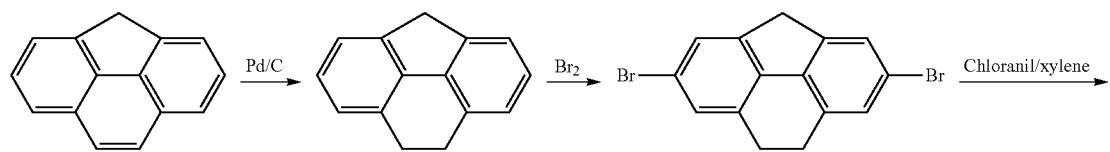
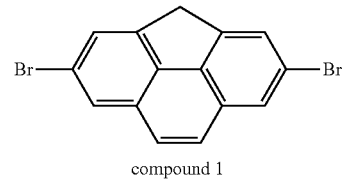
compound 1
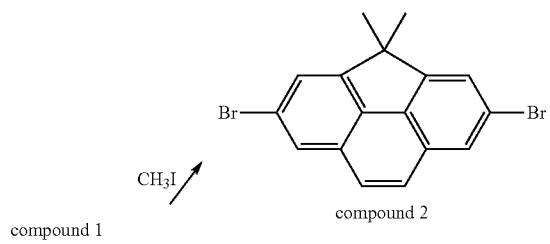
compound 2
compound 1
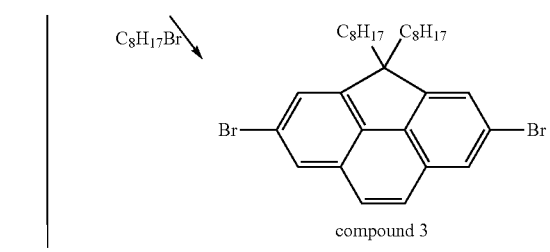
compound 3
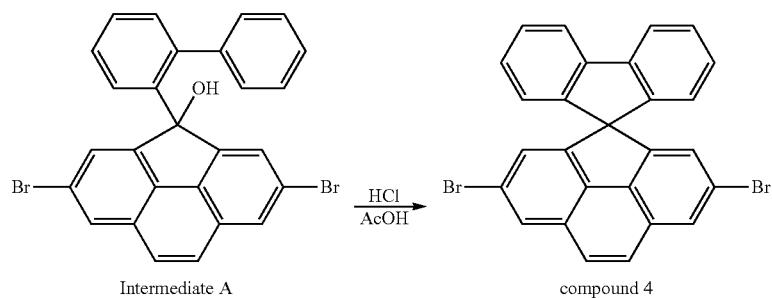
Intermediate A → compound 4
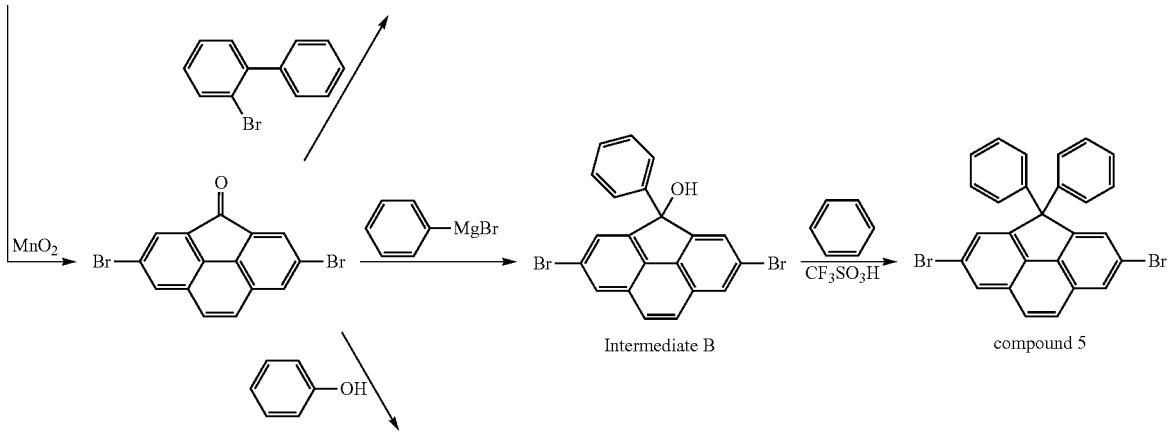
Intermediate B → compound 5

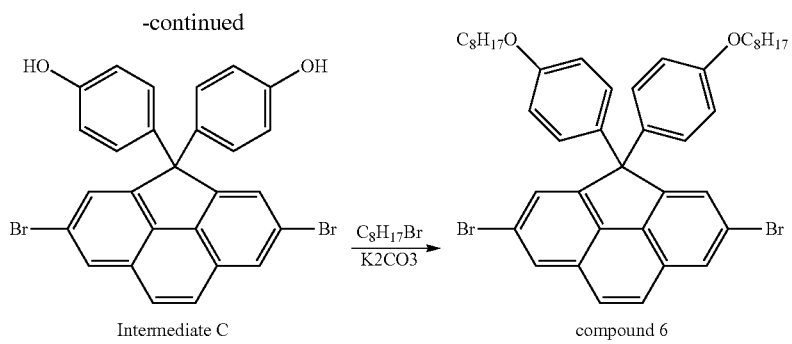

Synthesis Example 1

1) Synthesis of 8,9-dihydro-4H-cyclopenta[def]phenanthrene 4H-cyclopenta[def]phenanthrene (4.75 g, 25 mmol) was placed in a Par reactor bottle, and EtOH (200 ml) was added thereto. 5% Pd/C (3.99 g) was added to the reaction solution, and the resultant solution was incubated under a hydrogen pressure of 40 psi for 24 hours. After the reaction was terminated, the reaction solution was filtered, and the filtrate was concentrated under a reduced pressure to give a white product (4.42 g, 90%).

$^1$H NMR (300 MHz, CDCl$_3$, δ): 7.36 (2H, d), 7.21 (2H, t), 7.12 (2H, d), 3.90 (2H, s), 3.16 (4H, s)

2) Synthesis of 2,6-dibromo-8,9-dihydro-4H-cyclopenta[def]phenanthrene 8,9-dihydro-4H-cyclopenta[def]phenanthrene (4.42 g, 23 mmol) was placed in a 250 ml round bottom flask (RBF), and CCl$_4$ (100 ml) was added thereto. The reaction mixture was cooled to 0° C., and Br$_2$ (7.72 g, 48 mmol) was dropwise added thereto. The reaction solution was incubated for 4 hours and a 10% NaSO$_3$ solution was added thereto. The organic layer was separated, concentrated under a reduced pressure, and recrystallized from n-hexane to give a titled compound (4.45 g, 55%).

$^1$H NMR (300 MHz, CDCl$_3$, δ): 7.48 (2H, s), 7.28 (2H, s), 3.85 (2H, s), 3.10 (4H, s)

3) Synthesis of Compound 1

2,6-dibromo-8,9-dihydro-4H-cyclopenta[def]phenanthrene (4.45 g, 12.7 mmol) in a 250 ml round bottom flask was dissolved with xylene, and o-chloranil (4.15 g) was added thereto at room temperature. The reaction mixture was heated and refluxed in an oil bath for 72 hours. After the reaction was terminated, the reaction solution was cooled and concentrated under a reduced pressure. The residue was purified by silica gel column chromatography (mobile solvent: n-hexane) to give a compound 1 (3.6 g, 81%).

$^1$H NMR (300 MHz, CDCl$_3$, δ): 7.98 (2H, s), 7.79 (2H, s), 7.73 (2H, s), 4.28 (2H, s)

4) Synthesis of Compound 2

2,6-dibromo-4H-cyclopenta[def]phenanthrene (2.6 g, 7.7 mmol), t-BuOK (20.8 g, 61.6 mmol), DMSO (20 ml), and HMPA (20 ml) was placed in 50 ml round bottom flask with a syringe. The mixture was stirred for 50 minutes at room temperature and cooled to 0° C. CH$_3$I (3.75 ml, 61.6 mmol) was dropped to the mixture with a syringe and the resultant solution was stirred for 30 minutes at 0° C. Then, water (50 ml) and methylene chloride (50 ml) were added to the solution to separate an organic layer. The organic layer was purified by silica gel column chromatography to obtain compound 2 (3.6 g, 80%). $^1$H NMR (300 MHz, CDCl$_3$, δ): 7.98 (2H, s), 7.79 (2H, s), 7.73 (2H, s), 1.93 (m, 6H).

5) Synthesis of Material 1 (Formula 9)

The compound 2 (0.65 g, 1.747 mmol), bis(4-biphenyl)amine (TCI Corp.) (1.40 g, 4.37 mmol), sodium tert-butoxide (0.51 g, 0.5 mmol), Pd$_2$(dba)$_3$ [(tris(dibenzylidene acetone) dipalladium(0))] (0.08 g, 0.087 mmol), and tri(tert-butyl) phosphine (0.017 g, 0.087 mmol) in a 50 ml round bottom flask were dissolved with toluene (10 mL), and the reaction mixture was refluxed for 12 hours. After the reaction was terminated, the reaction solution was cooled to room temperature and extracted with distilled water (100 ml). The combined organic layers were dried over MgSO$_4$, concentrated, and purified by silica gel column chromatography. The eluate was concentrated and dried to give a material 1 represented by Formula 9 (1.1 g, yield: 75%).

$^1$H NMR (300 MHz, CDCl$_3$, δ): 7.90 (2H, s), 7.75 (2H, s), 7.72 (2H, s), 7.48-6.62 (m, 36H), 1.92 (m, 6H).

Synthesis Example 2

1) Synthesis of Compound 3

2,6-dibromo-4H-cyclopenta[def]phenanthrene (2.6 g, 7.7 mmol) and octyl bromide (3.6 g, 18.5 mmol) in a 50 ml round bottom flask were dissolved with toluene (10 ml), and TBAB (tetrabutylammoniumbromide) (0.125 g, 0.385 mmol) was added thereto. A solution of NaOH (3.1 g, 77 mmol) in water (50 ml) was added to the reaction mixture, and the resultant solution was refluxed for two days. After the reaction was terminated, the reaction solution was extracted with chloroform. The organic layer was dried over MgSO$_4$, concentrated, and purified by silica gel column chromatography (eluent: n-hexane). The eluate was distilled under a reduced pressure to remove unreacted octyl bromide, thereby giving a compound 2 (3.6 g, 80%).

¹H NMR (300 MHz, CDCl₃, δ): 7.98 (2H, s), 7.79 (2H, s), 7.73 (2H, s), 1.93 (m, 4H), 1.21 (m, 20H), 0.87 (m, 6H), 0.65 (broad s, 4H)

2) Synthesis of Material 2 (Formula 10)

The compound 2 (1 g, 1.747 mmol), diphenylamine (0.88 g, 5.241 mmol), sodium tert-butoxide (0.51 g, 0.5 mmol), Pd₂(dba)₃ [(tris(dibenzylidene acetone) dipalladium(0))] (0.08 g, 0.087 mmol), and tri(tert-butyl)phosphine (0.017 g, 0.087 mmol) in a 50 ml round bottom flask were dissolved with toluene (10 mL), and the reaction mixture was refluxed for 12 hours. After the reaction was terminated, the reaction solution was cooled to a room temperature and extracted with distilled water (100 ml). The combined organic layers were dried over MgSO₄, concentrated, and purified by silica gel column chromatography. The eluate was concentrated and dried to give a material 1 represented by Formula 9 (10.9 g, yield: 70%).

¹H NMR (300 MHz, CDCl₃, δ): 7.98-6.74 (m, 26H), 1.93 (m, 4H), 1.21 (m, 20H), 0.87 (m, 6H), 0.65 (broad s, 4H).

Synthesis Example 3

1) Synthesis of 2,6-dibromo-cyclopenta[def]phenanthren-4-one

Benzene (200 ml) was placed in a 250 ml round bottom flask, and the compound 1 (3.6 g, 10.4 mmol) was added thereto. MnO₂ (150 g) was added to the reaction mixture, and the resultant mixture was heated and refluxed in an oil bath for 18 hours. After the reaction was terminated, the reaction solution was filtered to remove MnO₂, and sufficiently washed with CHCl₃, THF, and MeOH in sequence. The filtrate was concentrated under a reduced pressure and the residue was recrystallized from acetone to give the titled compound (1.45 g, 39%).

¹H NMR (300 MHz, CDCl₃, δ): 8.08 (2H, s), 7.89 (2H, s), 7.74 (2H, s)

2) Synthesis of Intermediate A 2-bromobiphenyl (0.68 g, 2.95 mmol) was dissolved in anhydrous THF (10 ml), and the reaction mixture was cooled to −78° C. Then, t-BuLi (3.5 ml) was gradually dropwise added. The reaction mixture was stirred for one hour, and a solution of 2,6-dibromo-cyclopenta[def]phenanthren-4-one (1 g, 2.95 mmol) in anhydrous THF (5 ml) was dropwise added thereto for 30 minutes. After the reaction was terminated, the reaction solution was concentrated under a reduced pressure and extracted with ethylacetate and brine to separate an organic layer. The organic layer was concentrated and the residue was purified by silica gel column chromatography to give an intermediate A (3.6 g).

3) Synthesis of Compound 4

The intermediate A was dissolved in acetic acid (30 ml), and the reaction solution was cooled to 0° C. Then, HCl (1 ml) was dropwise added and the reaction mixture was incubated for two hours. After the reaction was terminated, the reaction solution was filtered and washed with acetic acid and methanol to give a white solid (2 g, 80%).

4) Synthesis of Material 3 (Formula 13)

A material 3 represented by Formula 13 was synthesized in the same manner as in the synthesis of the material 1 of Synthesis Example 1 except that the compound 4 was used instead of the compound 2 and 9H-carbazole was used instead of Bis(4-biphenyl)amine.

¹H NMR (300 MHz, CDCl₃, δ): 8.10-6.82 (m, 30H)

5) Synthesis of Material 4 (Formula 14)

The compound 4 (1 g, 1.747 mmol), di-naphthalene-2-yl-[4-(4,4,5,5-tetramethyl-[1,3,2]dioxaborane-2-yl)-phenyl]-amine (1.81 g, 3.843 mmol), K₂CO₃ (1.935 g, 0.014 mmol), tetrakis(triphenylphosphine)palladium (0) (0.4 g, 0.35 mmol), and tetrabutylammoniumbromide (1.13 g, 3.49 mmol) in a 50 ml round bottom flask were dissolved with toluene (10 ml) and THF (10 ml), and the reaction mixture was refluxed for 12 hours. After the reaction was terminated, the reaction solution was cooled to a room temperature and extracted with distilled water (100 ml) to separate an organic layer. The combined organic layers were dried over MgSO₄, concentrated, and purified by silica gel column chromatography. The eluate was concentrated and dried to give a material 4 represented by Formula 14 (0.8 g, yield: 45%).

¹H NMR (300 MHz, CDCl₃, δ): 8.15-6.54 (m, 50H)

Synthesis Example 4

1) Synthesis of Intermediate B 2,6-dibromo-cyclopenta[def]phenanthren-4-one (1.0 g, 2.76 mmol) was dissolved in dry ether (30 ml) and THF/10 ml), and phenyl magnesium bromide (3.0M in ether) was added slowly thereto and then the resultant mixture was refluxed for 3 hours. By adding water to the mixture, the reaction was terminated. 1N-HCl solution was added to the mixture until pH of the mixture to be 3-4 and the resultant was extracted with ethyl acetate. The organic layer was dried over anhydrous sodium sulfate, filtered and concentrated under a reduced pressure. The obtained solid was purified by silica gel column chromatography to give a desired compound (0.79 g, 65%).

2) Synthesis of Compound 5

The intermediate B (0.79 g, 1.79 mmol) was dissolved in dry benzene (20 ml) and trifluoromethane sulfonic acid (0.48 ml, 5.38 mmol, 3 eq.) was dropwise added thereto and then the mixture was stirred at 80° C. for 2 hours. The resultant was diluted with water, extracted with ethyl acetate. The organic layer was dried over anhydrous magnesium sulfate, filtered and concentrated to obtain a solid. The obtained solid was purified by silica gel column chromatography to give a desired compound (0.65 g, 63%).

¹H NMR (300 MHz, CDCl₃, δ): 7.22-7.26 (m, 10H), 7.70 (s, 2H), 7.80 (s, 3H), 8.00 (s, 2H)

3) Synthesis of Material 5 (Formula 15)

A material 5 represented by Formula 15 was synthesized in the same manner as in the synthesis of the material 1 of Synthesis Example 1 except that the compound 5 was used instead of the compound 2, and 9H-carbazole was used instead of bis(4-biphenyl)amine.

$^1$H NMR (300 MHz, CDCl$_3$, δ): 8.02-6.89 (m, 32H).

4) Synthesis of Material 6 (Formula 27)

A material 6 represented by Formula 27 was synthesized in the same manner as in the synthesis of the material 1 of Synthesis Example 1 except that the compound 5 was used instead of the compound 2.

1H NMR (300 MHz, CDCl3, δ): 8.05-7.75 (6H, m), 7.55-6.68 (m, 36H).

5) Synthesis of Material 7 (Formula 35)

4-bromo triphenylamine 7.6 g (23.45 mmol), aniline 21.85 g (0.235 mol), sodium tert-butoxide 6.76 g (70 mmol). Pd$_2$(dba)$_3$[(tris(dibenzilidene acetone)dipalladium(0))]0.86 g (0.938 mmol) and tri(tert-butyl)phosphine 0.23 g (1.173 mmol) in 500 ml round bottom flask were dissolved with toluene 200 ml, and refluxed for 12 hours. After the reaction was terminated, the reaction solution was cooled to room temperature, and 200 ml of distilled water was added thereto to extract an organic layer. The organic layer was dried over MgSO$_4$, concentrated, and purified by silica gel column chromatography. The eluate was concentrated and dried to give N,N,N'-triphenyl-p-phenylenediamine (6.71 g, 85%).

The obtained N,N,N'-triphenyl-p-phenylenediamine (3.36 g, 10.0 mmol), compound 5 (2.0 g, 4.0 mmol), sodium tert-butoxide (1.15 g, 12 mmol), Pd$_2$(dba)$_3$[(tris(dibenzylidene acetone)dipalladium(0))] (0.14 g, 0.16 mmol) and tri(tert-butyl)phosphine (0.04 g, 0.2 mmol) in 100 ml round bottom flask were dissolved with 50 ml of toluene and refluxed for 12 hours. After the reaction was terminated, the reaction solution was cooled to room temperature and 50 ml of distilled water was added thereto to extract an organic layer. The obtained organic layer was dried over MgSO$_4$, concentrated, and purified by silica gel column chromatography. The eluate was concentrated and dried to give material 7 represented by Formula 35 (2.91 g, yield: 72%).

$^1$H NMR (300 MHz, CDCl$_3$, δ): 7.86-7.71 (6H, m), 7.32-6.64 (m, 48H).

Synthesis Example 5

1) Synthesis of Intermediate C 2,6-dibromo-cyclopenta[def]phenanthren-4-one (0.95 g, 2.62 mmol) and phenol (30 ml) were added to a 250 ml 3-neck round bottom flask. The reaction mixture was heated and incubated for five hours while a HCl gas was run into the mixture. After the reaction was terminated, the reaction solution was concentrated under a reduced pressure to remove unreacted phenol. The residue was purified by silica gel column chromatography to give an intermediate C (0.59 g, 42%).

2) Synthesis of Compound 6

The intermediate C (0.95 g, 2.62 mmol) was placed in a 100 ml round bottom flask, and DMF (5 ml) and acetonitrile (20 ml) were added thereto. K$_2$CO$_3$ (1.52 g) and octyl bromide (2.11 g) were sequentially added, and the reaction mixture was heated and refluxed for 18 hours. After the reaction was terminated, the organic layer was separated and purified by silica gel column chromatography to give a compound 4 (0.68 g, 82%).

$^1$H NMR (300 MHz, CDCl$_3$, δ): 7.78 (2H, d) 7.79 (2H, s) 7.67 (2H, d) 7.11 (4H, dd) 3.89 (4H, t) 1.74 (4H, q) 1.28 (20H, m) 0.88 (6H, m)

4) Synthesis of Material 8 (Formula 38)

A material 8 represented by Formula 38 was synthesized in the same manner as in the synthesis of the material 1 of Synthesis Example 1 except that the compound 6 was used instead of the compound 2, and 9H-carbazole was used instead of bis(4-biphenyl)amine.

$^1$H NMR (300 MHz, CDCl$_3$, δ): 7.85-6.92 (30H, m) (4H, dd) 3.89 (4H, t) 1.74 (4H, q) 1.28 (20H, m) 0.88 (6H, m)

5) Synthesis of Material 9 (Formula 39)

A material 9 represented by Formula 39 was synthesized in the same manner as in the synthesis of the material 4 of Synthesis Example 3 except that the compound 6 was used instead of the compound 4.

$^1$H NMR (300 MHz, CDCl$_3$, δ): 7.95-6.75 (50H, m) (4H, dd) 3.89 (4H, t) 1.74 (4H, q) 1.28 (20H, m) 0.88 (6H, m)

Evaluation Example

Evaluation of Optical Characteristics of Materials 1-5

The photoluminescence (PL) spectra of the materials in a solution phase and a film phase were measured to evaluate the emission characteristics of the materials.

In order to evaluate optical characteristics of a solution phase, each of the materials 3, 4, 8 and 9 was diluted to a concentration of 10 mM with toluene, and the PL spectra of the diluted solutions were measured using an ISC PC1 spectrofluorometer equipped with a xenon lamp. Also, in order to evaluate optical characteristics of a film phase, quartz substrates were prepared and washed with acetone and pure water. Then, the materials 3, 4, 8 and 9 were spin-coated on the substrates and heated at 110° C. for 30 minutes to form films with a thickness of 1,000 Å. The PL spectra of the films were measured. The results are presented in Table 1 below. As shown in Table 1, it can be seen that the materials according to the present invention have emission characteristics suitable for organic EL devices.

TABLE 1

| Material | Solution ($\lambda_{max}$)(nm) | Film ($\lambda_{max}$)(nm) |
| --- | --- | --- |
| 3 | 390 | 397 |
| 4 | 420 | 445 |
| 8 | 395 | 398 |
| 9 | 420 | 450 |

Example 1

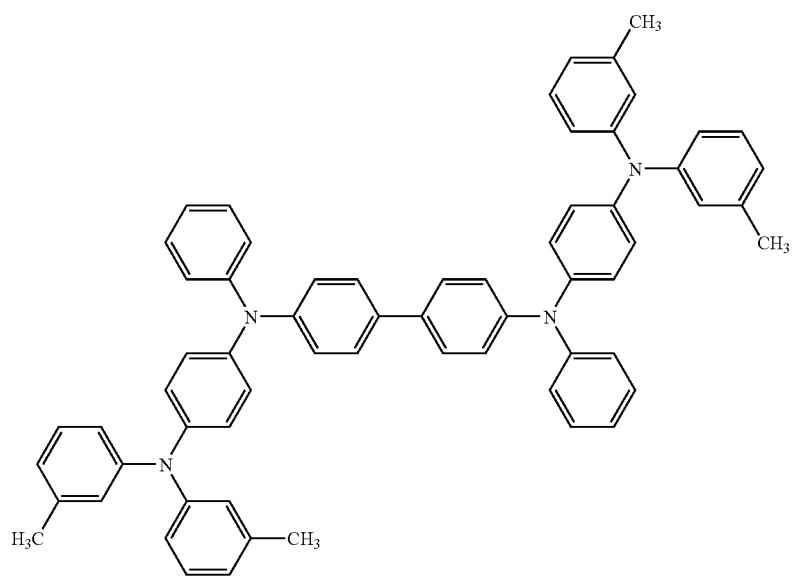

<Formula 47>

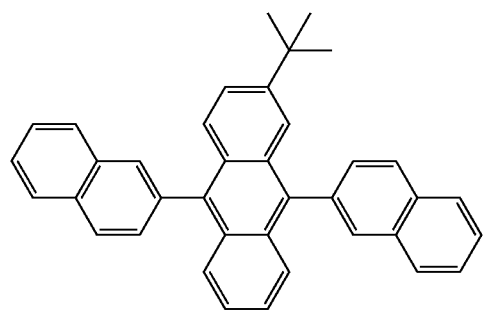

<Formula 48>

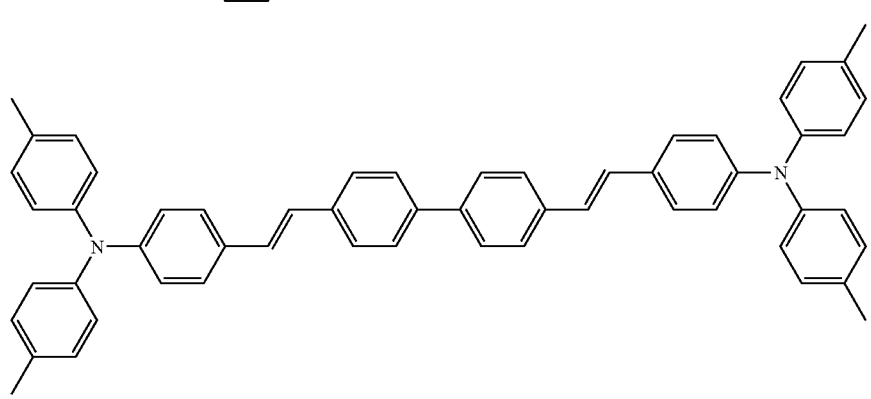

<Formula 49>

Organic EL devices having the following structure were manufactured using the material 1 as a hole transport layer, the compound of Formula 47 as a hole injection layer, the compound of Formula 48 as host of the light-emitting layer and the compound of Formula 49 as a dopant of the light-emitting layer: ITO/Formula 47 (200 Å)/material 1 (300 Å)/Formula 48: Formula 49 (300 Å)/Alq3 (40 Å)/LiF (10 Å)/Al (2000 Å).

A 15Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. The compound of Formula 47 (hole injection layers) and the material 1 (hole transport layers) were vacuum deposited on the anodes. A mixture of the compound of Formula 48 and the compound of Formula 49 (weight ratio of 100:5) was vacuum deposited to form light-emitting layers. Then, an Alq3 compound was vacuum deposited to a thickness of 40 Å on the light-emitting layers to form electron transport layers. LiF (10 Å, electron injection layers) and Al (2000 Å, cathodes) were sequentially vacuum-deposited on the electron transport layers to thereby complete organic EL devices as shown in FIG. 1A. The organic EL devices exhibited red emission of 14,000 cd/m² at a voltage of 6.0V and efficiency of 5.45 cd/A.

Example 2

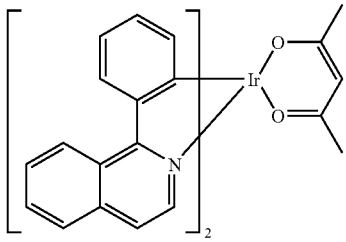

<Formula 50>

Organic EL devices having the following structure were manufactured using the material 3 as a host of a light-emitting layer and the compound of Formula 50 as a dopant of the light-emitting layer: ITO/Formula 47 (200 Å)/α-NPD (300 Å)/material 3: Formula 50 (300 Å)/Alq3 (40 Å)/LiF (10 Å)/Al (2000 Å).

Figure 2A:
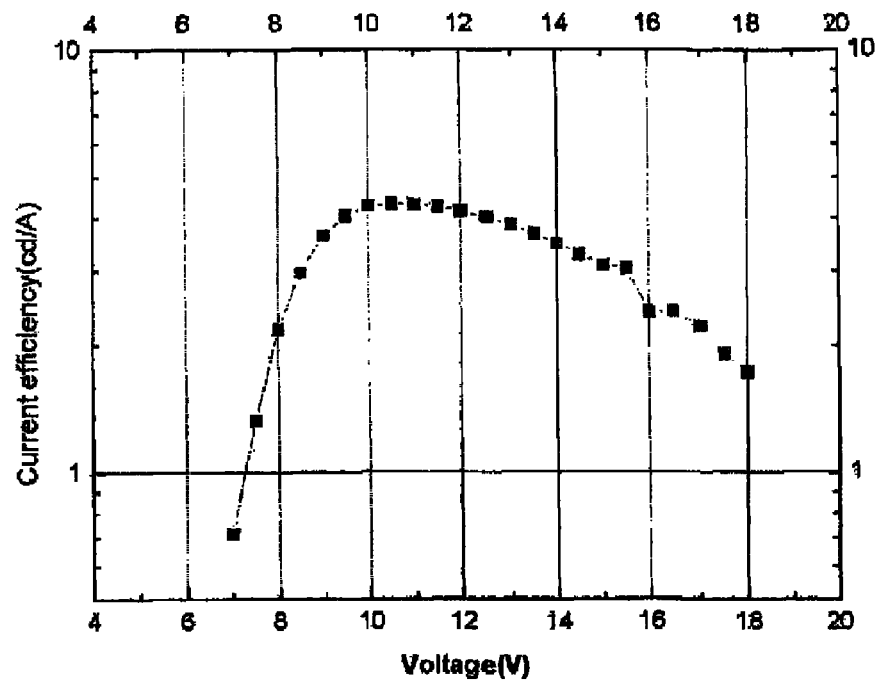
FIGS. 2A and 2B are graphs illustrating voltage-efficiency characteristics of organic EL devices according to embodiments of the present invention.

A 15Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. The compound of Formula 47 (hole injection layers) and α-NPD (hole transport layers) were vacuum deposited on the anodes. A mixture of the material 3 and RD15 (Formula 50) (weight ratio of 100:10) was vacuum deposited to form light-emitting layers. Then, an Alq3 compound was vacuum deposited to a thickness of 40 Å on the light-emitting layers to form electron transport layers. LiF (10 Å, electron injection layers) and Al (2000 Å, cathodes) were sequentially vacuum-deposited on the electron transport layers to thereby complete organic EL devices as shown in FIG. 1A. The organic EL devices exhibited red emission of 1200 cd/m² at a voltage of 10V and efficiency of 4.32 cd/A. The voltage-efficiency characteristics of the organic EL devices are illustrated in FIG. 2A.

Example 3

Organic EL devices having the following structure were manufactured in the same manner as in Example 1 except that α-NPD was used as a hole transport layer and the material 4 as a dopant of the light-emitting layer: ITO/Formula 47 (200 Å)/α-NPD (300 Å)/Formula 48: material 4 (300 Å)/Alq3 (40 Å)/LiF (10 Å)/Al (2000 Å). The organic EL devices exhibited blue emission of 4600 cd/m² at a voltage of 8V and efficiency of 5.4 cd/A.

Example 4

Organic EL devices having the following structure were manufactured in the same manner as in Example 2 except that the material 5 was used as a host of a light-emitting layer: ITO/Formula 47 (200 Å)/α-NPD (300 Å)/material 5:Formula 50 (300 Å)/Alq3 (40 Å)/LiF (10 Å)/Al (2000 Å). The organic EL devices exhibited blue emission of 6500 cd/m² at a voltage of 10V and efficiency of 7.48 cd/A.

Example 5

Organic EL devices having the following structure were manufactured in the same manner as in Example 1 except that the material 6 as a hole transport layer: ITO/Formula 47 (200 Å)/material 6 (300 Å)/Formula 48: Formula 49 (300 Å)/Alq3 (40 Å)/LiF (10 Å)/Al (2000 Å). The organic EL devices exhibited blue emission of 15,800 cd/m² at a voltage of 6.5V and efficiency of 7.66 cd/A.

Example 6

Organic EL devices having the following structure were manufactured in the same manner as in Example 1 except that the material 7 was used as hole injection layer and α-NPD as a hole transport layer: ITO/material 7 (200 Å)/α-NPD (300 Å)/Formula 48:Formula 49 (300 Å)/Alq3 (40 Å)/LiF (10 Å)/Al (2000 Å). The organic EL devices exhibited blue emission of 15,000 cd/m² at a voltage of 6.0V and efficiency of 6.48 cd/A.

Example 7

Organic EL devices having the following structure were manufactured using the material 8 as a host of light-emitting layer and the compound of Formula 50 as a dopant of light-emitting layer: ITO/PEDOT (400 Å)/material 8:Formula 50 (300 Å)/Alq3 (40 Å)/LiF (10 Å)/Al (2000 Å).

Figure 2B:
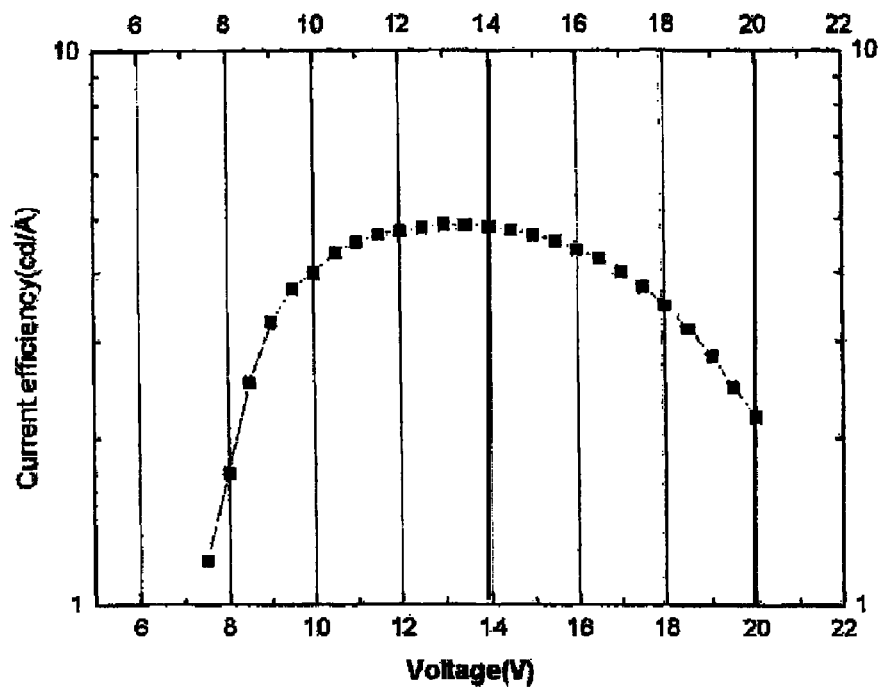

A 15Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. PEDOT-PSS (Al4083) (Bayer) was coated on the anodes and heated in air at 110° C. for 5 minutes and then in a nitrogen atmosphere at 200° C. for 5 minutes to form hole injection layers with a thickness of 400 Å. A mixture of the material 8 (0.1 g) as a host and the compound of Formula 50 (0.01 g) as a dopant (10 parts by weight of the compound of Formula 50 based on 100 parts by weight of the material 8) was spin-coated on the hole injection layers and heated at 100° C. for 30 minutes to form light-emitting layers with a thickness of 300 Å. Then, an Alq3 compound was vacuum deposited to a thickness of 40 Å on the light-emitting layers to form electron transport layers. LiF (10 Å, electron injection layers) and Al (2000 Å, cathodes) were sequentially vacuum-deposited on the electron transport layers to thereby complete organic EL devices as shown in FIG. 1B. The organic EL devices exhibited red emission of 1500 cd/m² at a voltage of 9V and efficiency of 4.1 cd/A. The voltage-efficiency characteristics of the organic EL devices are illustrated in FIG. 2B.

Example 8

Organic EL devices having the following structure were manufactured in the same manner as in Example 7 except that the compound of Formula 48 was used as a host of a light-emitting layer, and the material 9 as a dopant of the light-emitting layer: ITO/PEDOT (400 Å)/Formula 48: material 9 (300 Å)/Alq3 (40 Å)/LiF (10 Å)/Al (2000 Å). The organic EL devices exhibited blue emission of 3700 cd/m² at a voltage of 6V and efficiency of 4.2 cd/A.

From the above Examples, it can be seen that the materials of the present invention have good EL characteristics as phosphorescent and fluorescent materials.

A compound of Formula 1 according to the present invention is available for both dry and wet processes, and has good emission characteristics and thermal stability. Therefore, the use of the compound of the present invention enables to produce an organic EL device having a low driving voltage and good color purity and efficiency.

What is claimed is:

1. An organic compound represented by Formula 1:

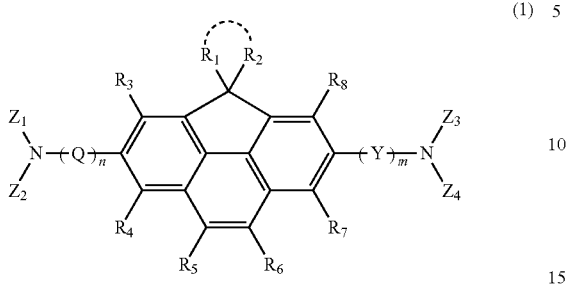

(1)

wherein Y and Q are the same or different and each is a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5;

n is an integer of 0 to 5;

$R_3$, $R_4$, $R_5$, $R_6$, $R_7$, and $R_8$ are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($G_1$)($G_2$), or —Si($G_3$)($G_4$)($G_5$) where $G_1$, $G_2$, $G_3$, $G_4$, and $G_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group; and $R_1$ and $R_2$ together or independently form a substituted or unsubstituted non-heterocyclic ring, and $Z_1$, $Z_2$, $Z_3$, and $Z_4$ are substituted or unsubstituted non-heterocyclic rings, wherein at least one of m and n is not 0.

2. The organic compound of claim 1, wherein in Formula 1, $R_1$ and $R_2$ are linked together to form one of the rings represented by Formulae 2 through 5:

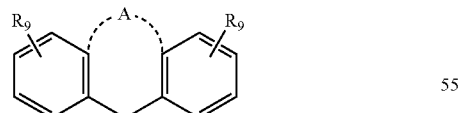

(2)

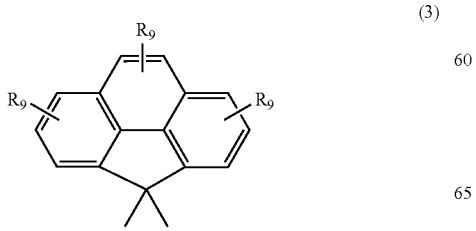

(3)

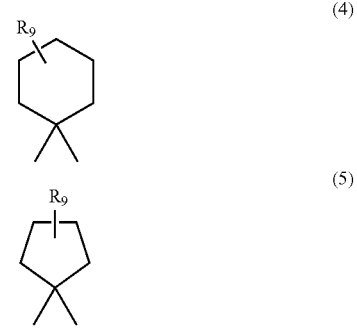

(4)

(5)

wherein "$R_9$"s are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, —N($G_1$)($G_2$), or —Si($G_3$)($G_4$)($G_5$) where $G_1$, $G_2$, $G_3$, $G_4$, and $G_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group; and A is a single bond, or —($CH_2$)$_s$—, where s is an integer of 1 to 5.

3. The organic compound of claim 1, which is selected from the group consisting of compounds represented by Formulae 6 through 8 below:

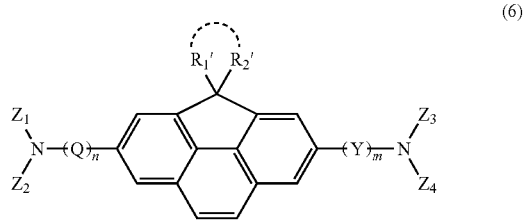

(6)

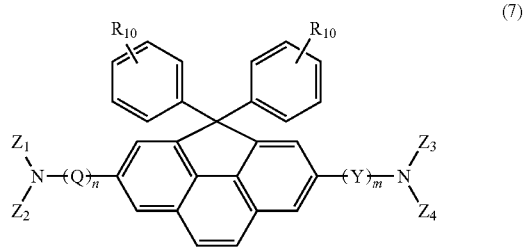

(7)

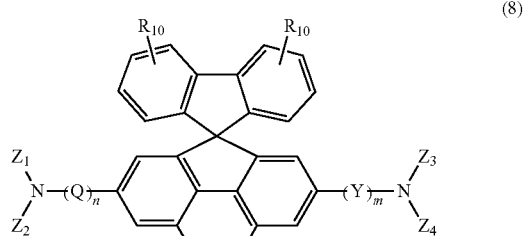

(8)

wherein Y and Q are the same or different and each is a substituted or unsubstituted C2-C30 alkylene group, a substituted or unsubstituted C6-C30 cycloalkylene group, a substituted or unsubstituted C6-C30 arylene group, a substituted or unsubstituted C2-C30 heteroarylene group, or a substituted or unsubstituted C2-C30 alkenylene group;

m is an integer of 0 to 5;

n is an integer of 0 to 5;

$R_1'$ and $R_2'$ together or independently form a substituted or unsubstituted non-heterocyclic ring, and $Z_1$, $Z_2$, $Z_3$, and $Z_4$ are independently substituted or unsubstituted non-heterocyclic rings; and "$R_{10}$"s are the same or different and each is a hydrogen, a halogen, a cyano group, a hydroxyl group, a substituted or unsubstituted C1-C20 alkyl group, a substituted or unsubstituted C3-C20 cycloalkyl group, a substituted or unsubstituted C2-C30 heterocycloalkyl group, a substituted or unsubstituted C1-C20 alkoxy group, a substituted or unsubstituted C6-C30 aryl group, a substituted or unsubstituted C6-C30 aralkyl group, a substituted or unsubstituted C2-C30 heteroaryl group, $-N(G_1)(G_2)$, or $-Si(G_3)(G_4)(G_5)$ where $G_1$, $G_2$, $G_3$, $G_4$, and $G_5$ are each independently a hydrogen, a substituted or unsubstituted C1-C20 alkyl group, a substituted or unsubstituted C6-C30 aryl group, a substituted or unsubstituted C2-C30 heteroaryl group, a substituted or unsubstituted C5-C20 cycloalkyl group, or a substituted or unsubstituted C2-C30 heterocycloalkyl group, wherein at least one of m and n is not 0.

4. The organic compound of claim 1, which is one of compounds represented by Formulae 14, 18-21, 37 and 39:

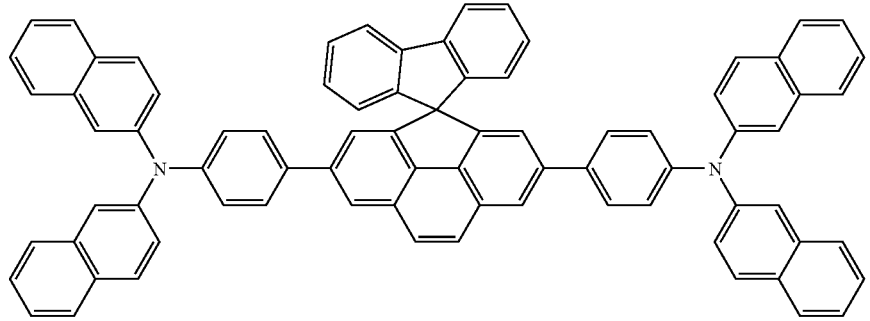

(14)

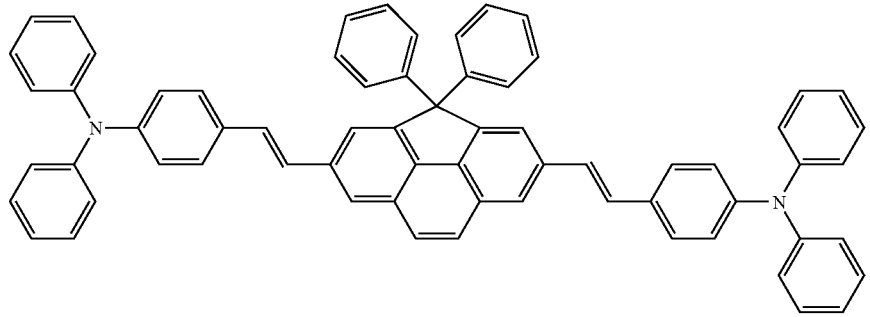

(18)

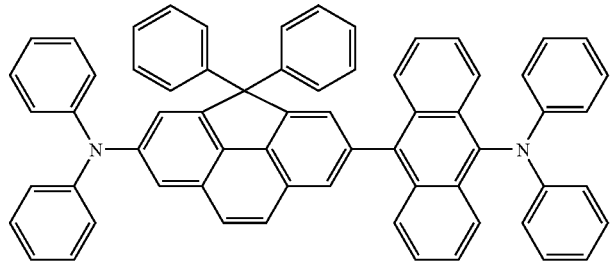

(19)

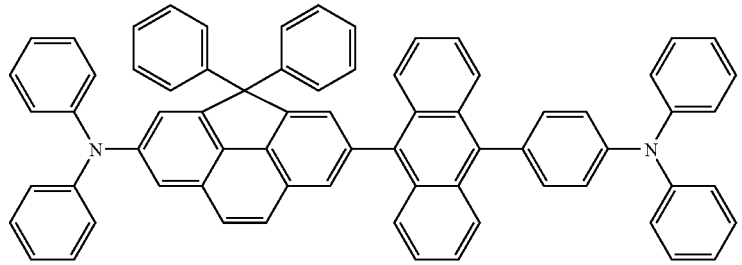

(20)

-continued
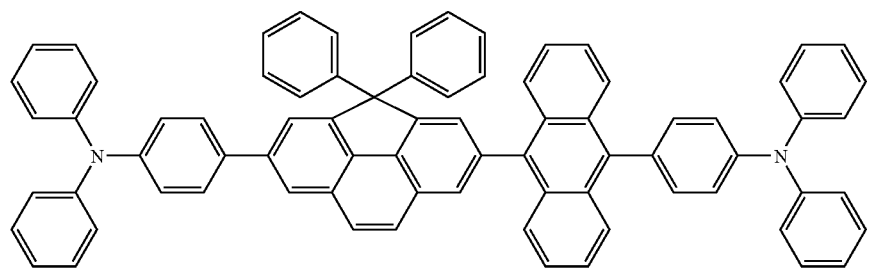
(21)
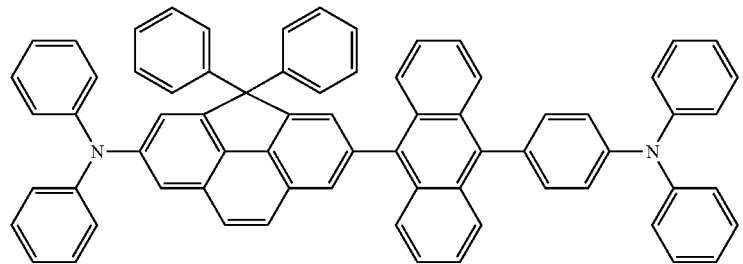
(37)
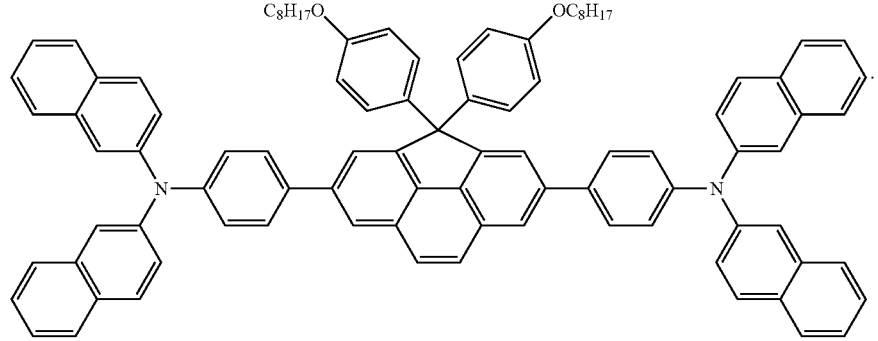
(39)
* * * * *